US010788492B2

(12) United States Patent
Shenk et al.

(10) Patent No.: US 10,788,492 B2
(45) Date of Patent: Sep. 29, 2020

(54) SIRT4 LIPOAMIDASE ACTIVITY AND USES THEREOF

(71) Applicant: THE TRUSTEES OF PRINCETON UNIVERSITY, Princeton, NJ (US)

(72) Inventors: Thomas Shenk, Princeton, NJ (US); Todd M. Greco, Langhorne, PA (US); Ileana M. Cristea, Princeton, NJ (US); Rommel A. Mathias, Plainsboro, NJ (US); Adam Oberstein, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 412 days.

(21) Appl. No.: 15/106,932

(22) PCT Filed: Jan. 15, 2015

(86) PCT No.: PCT/US2015/011585
§ 371 (c)(1),
(2) Date: Jun. 21, 2016

(87) PCT Pub. No.: WO2015/109082
PCT Pub. Date: Jul. 23, 2015

(65) Prior Publication Data
US 2019/0094225 A1 Mar. 28, 2019

Related U.S. Application Data

(60) Provisional application No. 62/091,167, filed on Dec. 12, 2014, provisional application No. 61/927,799, filed on Jan. 15, 2014.

(51) Int. Cl.
*C12Q 1/34* (2006.01)
*G01N 33/573* (2006.01)

(52) U.S. Cl.
CPC ............ *G01N 33/573* (2013.01); *C12Q 1/34* (2013.01); *G01N 2333/90212* (2013.01); *G01N 2333/91057* (2013.01); *G01N 2500/00* (2013.01)

(58) Field of Classification Search
None
See application file for complete search history.

(56) References Cited

U.S. PATENT DOCUMENTS 8,304,206 B2 11/2012 Smith et al.

OTHER PUBLICATIONS

Mathias et al, Sirtuin 4 Is a Lipoamidase Regulating Pyruvate Dehydrogenase Complex Activity. Cell 159, 1615-1625, Dec. 18, 2014.*
Ahuja et al., Regulation of insulin secretion by SIRT4, a mitochondrial ADP-ribosyltransferase, J. Biol. Chem., 282(46):33583-92 (2007).
Cristea et al., Fluorescent proteins as proteomic probes, Mol. Cell Proteomics, 4(12):1933-41 (2005).
Csibi et al., The mTORC1 pathway stimulates glutamine metabolism and cell proliferation by repressing SIRT4, Cell, 153(4):840-54 (2013).
Du et al., Sirt5 is a NAD-dependent protein lysine demalonylase and desuccinylase, Science, 334(6057):806-9 (2011).
Feldman et al., Activation of the protein deacetylase SIRT6 by long-chain fatty acids and widespread deacylation by mammalian sirtuins, J. Biol. Chem., 288(43):31350-6 (2013).
Guarente, Sir2 links chromatin silencing, metabolism, and aging, Genes Dev., 14(9):1021-6 (2000).
Haigis et al., SIRT4 inhibits glutamate dehydrogenase and opposes the effects of calorie restriction in pancreatic beta cells, Cell, 126(5):941-54 (2006).
Imai et al., Transcriptional silencing and longevity protein Sir2 is an NAD-dependent histone deacetylase, Nature, 403(6771):795-800 (2000).
International Preliminary Report on Patentability, International Application No. PCT/US2015/011585, dated Jul. 19, 2016.
International Search Report and Written Opinion, International Application No. PCT/US15/11585, dated Apr. 27, 2015.
Ishihama et al., Modular stop and go extraction tips with stacked disks for parallel and multidimensional Peptide fractionation in proteomics, J. Proteome Res., 5(4):988-94 (2006).
Jeong et al., SIRT4 has tumor-suppressive activity and regulates the cellular metabolic response to DNA damage by inhibiting mitochondrial glutamine metabolism, Cancer Cell, 23(4):450-63 (2013).
Jeong et al., SIRT4 protein suppresses tumor formation in genetic models of Myc-induced B cell lymphoma, J. Biol. Chem., 289(7):4135-44 (2014).
Jiang et al., SIRT6 regulates TNF—a secretion through hydrolysis of long-chain fatty acyl lysine, Nature, 496(7443):110-3 (2013).
Joshi et al., The functional interactome landscape of the human histone deacetylase family, Mol. Syst. Biol., 9:672 (2013).
Laurent et al., SIRT4 coordinates the balance between lipid synthesis and catabolism by repressing malonyl CoA decarboxylase, Mol. Cell., 50(5):686-98 (2013).
Lin et al., Protein lysine acylation and cysteine succination by intermediates of energy metabolism, ACS Chem. Biol., 7(6):947-60 (2012).

(Continued)

*Primary Examiner* — Sheridan Swope
(74) *Attorney, Agent, or Firm* — Marshall, Gerstein & Borun LLP

(57) ABSTRACT

The present application demonstrates that sirtuin 4 (SIRT4) acts as a cellular lipoamidase that negatively regulates pyruvate dehydrogenase complex (PDHC) activity through hydrolysis of its lipoamide cofactors.

12 Claims, 21 Drawing Sheets

Specification includes a Sequence Listing.

(56) References Cited

OTHER PUBLICATIONS

Linn et al., Alpha-keto acid dehydrogenase complexes. X. Regulation of the activity of the pyruvate dehydrogenase complex from beef kidney mitochondria by phosphorylation and dephosphorylation, Proc. Natl. Acad. Sci. USA, 62(1):234-41 (1969).

Lombard et al., Mammalian Sir2 homolog SIRT3 regulates global mitochondrial lysine acetylation, Mol. Cell Biol., 27(24):8807-14 (2007).

Mathias et al., Sirtuin 4 is a lipoamidase regulating pyruvate dehydrogenase complex activity, Cell, 159(7):1615-25 (2014).

Michishita et al., Evolutionarily conserved and nonconserved cellular localizations and functions of human SIRT proteins, Mol. Biol. Cell, 16(10):4623-35 (2005).

NCBI Reference Sequence: NP_036372.1, NAD-dependent protein lipoamidase sirtuin-4, mitochondrial [*Homo sapiens*], Apr. 8, 2017.

Newman et al., Mitochondrial protein acylation and intermediary metabolism: regulation by sirtuins and implications for metabolic disease, J. Biol. Chem., 287(51):42436-43 (2012).

Nilsson et al., Co-purification of human serum lipoamidase and biotinidase: evidence that the two enzyme activities are due to the same enzyme protein, Biochem. J., 291(Pt. 2):545-51 (1993).

Nilsson et al., Lipoamidase and biotinidase activiites in the rat: tissue distribution and intracellular localization, Clin. Chem. Lab. Med., 32(7):501-9 (1994).

Peng et al., The first identification of lysine malonylation substrates and its regulatory enzyme, Mol. Cell Proteomics, 10(12):M111.012658 (2011).

Perham, Domains, motifs, and linkers in 2-oxo acid dehydrogenase multienzyme complexes: a paradigm in the design of a multifunctional protein, Biochemistry, 30(35):8501-12 (1991).

Picotti et al., Selected reaction monitoring-based proteomics: workflows, potential, pitfalls and future directions, Nat. Methods, 9(6):555-66 (2012).

Rauh et al., An acetylome peptide microarray reveals specificities and deacetylation substrates for all human sirtuin isoforms, Nat. Commun., 4:2327 (2013).

Roche et al., Sizing of bovine heart and kidney pyruvate dehydrogenase complex and dihydrolipoyl transacetylase core by quasielastic light scattering, Biochemistry, 32(21):5629-37 (1993).

Tsai et al., Functional proteomics establishes the interaction of SIRT7 with chromatin remodeling complexes and expands its role in regulation of RNA polymerase I transcription, Mol. Cell Proteomics, 11(5):60-76 (2012).

Verdin et al., Sirtuin regulation of mitochondria: energy production, apoptosis, and signaling, Trends Biochem. Sci., 35(12):669-75 (2010).

Wagenknecht et al., Cryoelectron microscopy of mammalian pyruvate dehydrogenase complex, J. Biol. Chem., 266(36):24650-6 (1991).

Wang et al., Activity assay of lipoamidase, an expected modulator of metabolic fate of externally administered lipoic acid, Inflammation and Regeneration, 31(1):88-94 (2011).

Wieland et al., ATP-dependent inactivation of heart muscle pyruvate dehydrogenase and reactivation by Mg(++), FEBS Lett., 3(4):271-4 (1969).

Wirth et al., Mitochondrial SIRT4-type proteins in Caenorhabditis elegans and mammals interact with pyruvate carboxylase and other acetylated biotin-dependent carboxylases, Mitochondrion, 13(6):705-20 (2013).

Zhou et al., The remarkable structural and functional organization of the eukaryotic pyruvate dehydrogenase complexes, Proc. Natl. Acad. Sci. USA, 98(26):14802-7 (2001).

* cited by examiner

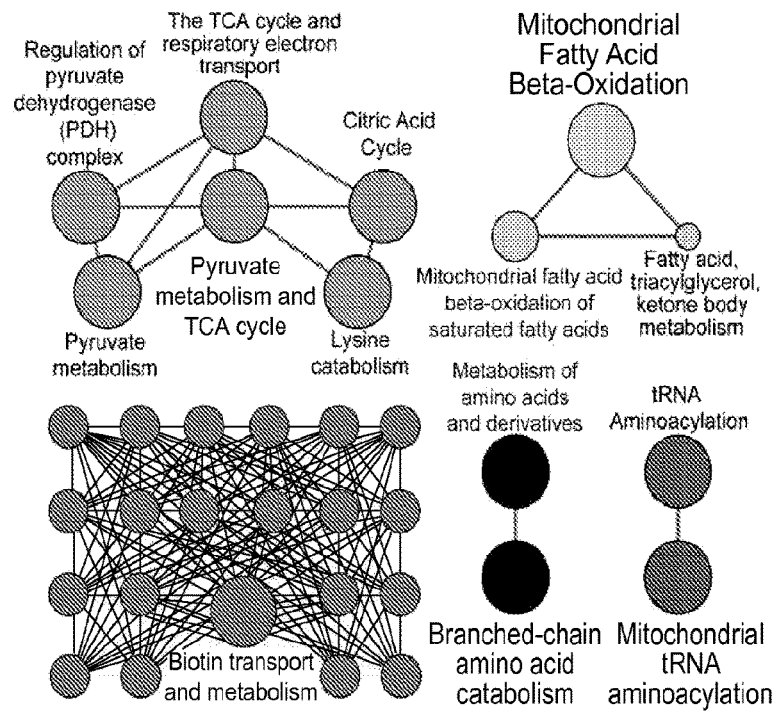
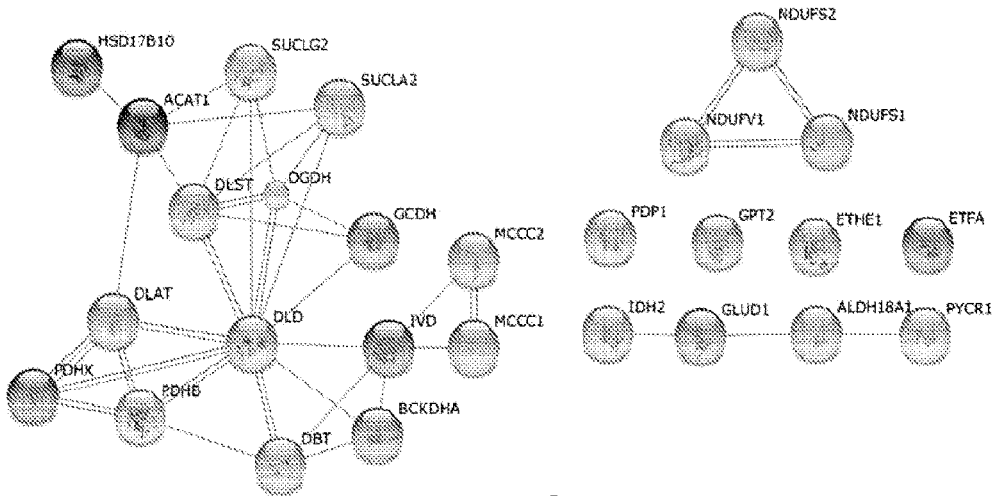
FIG. 4

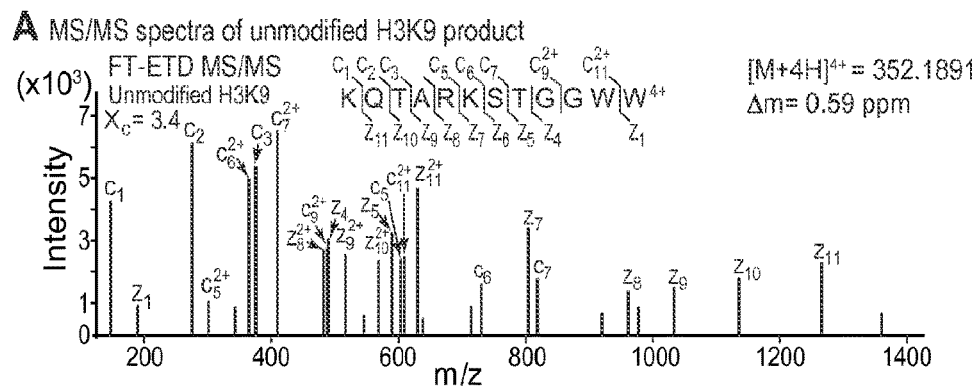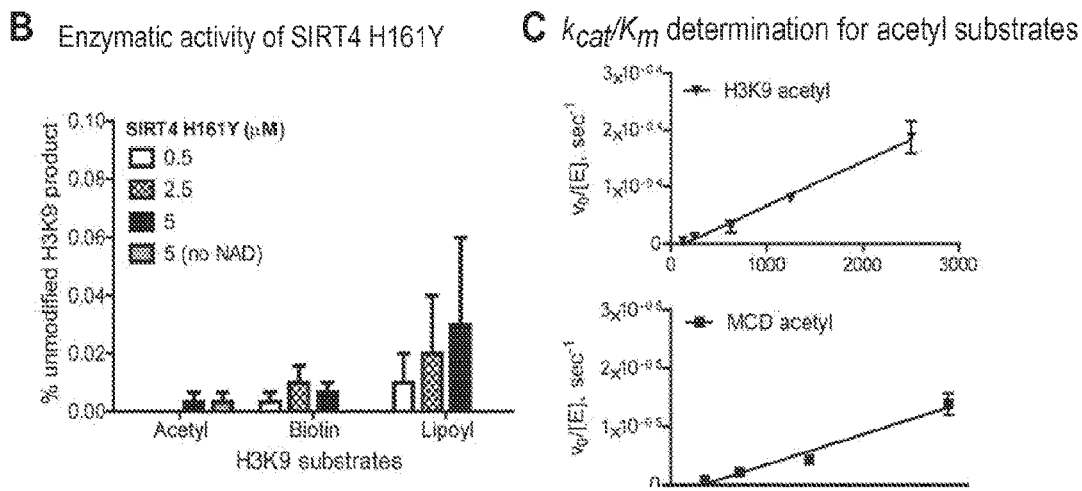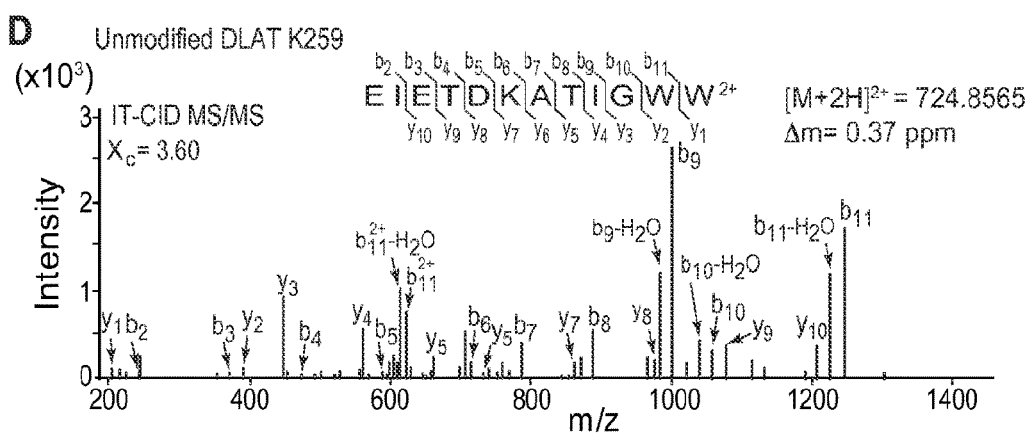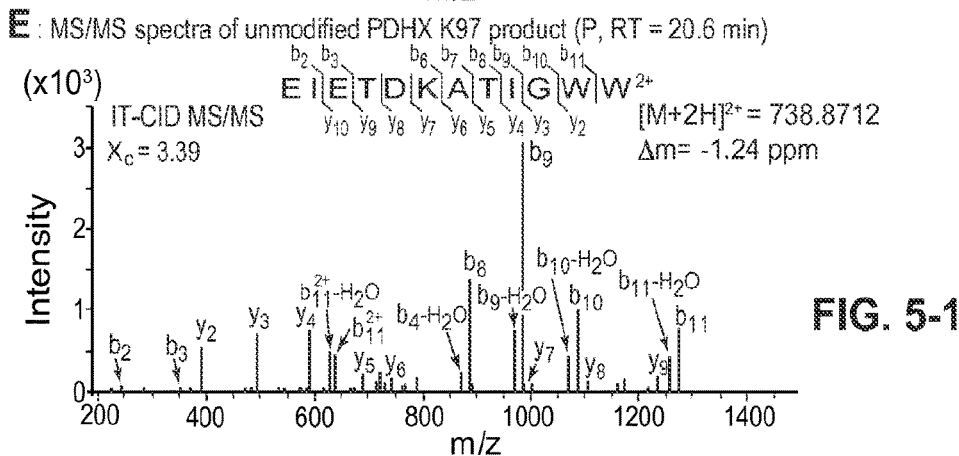
FIG. 5-1

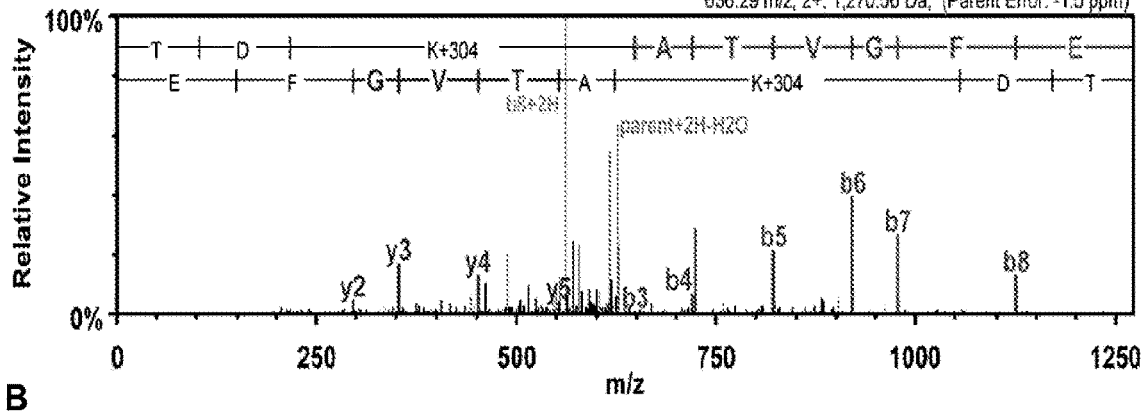
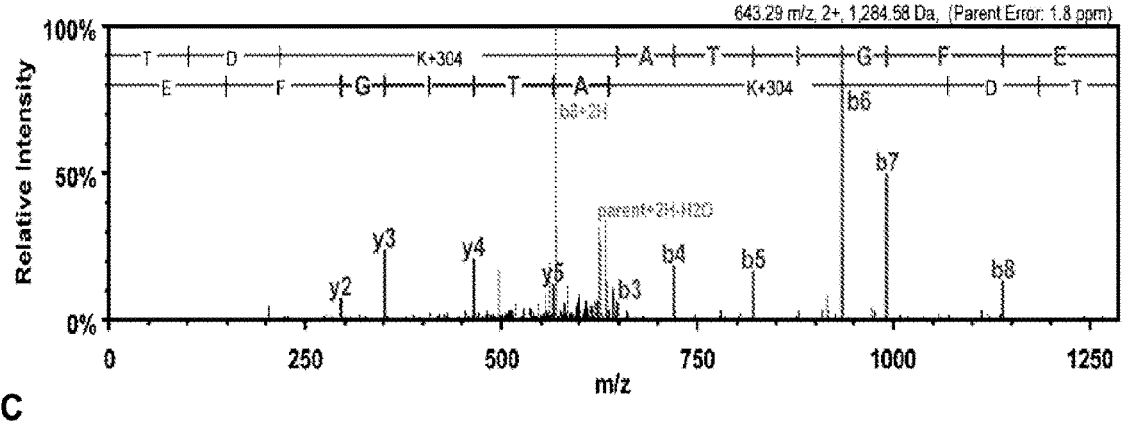
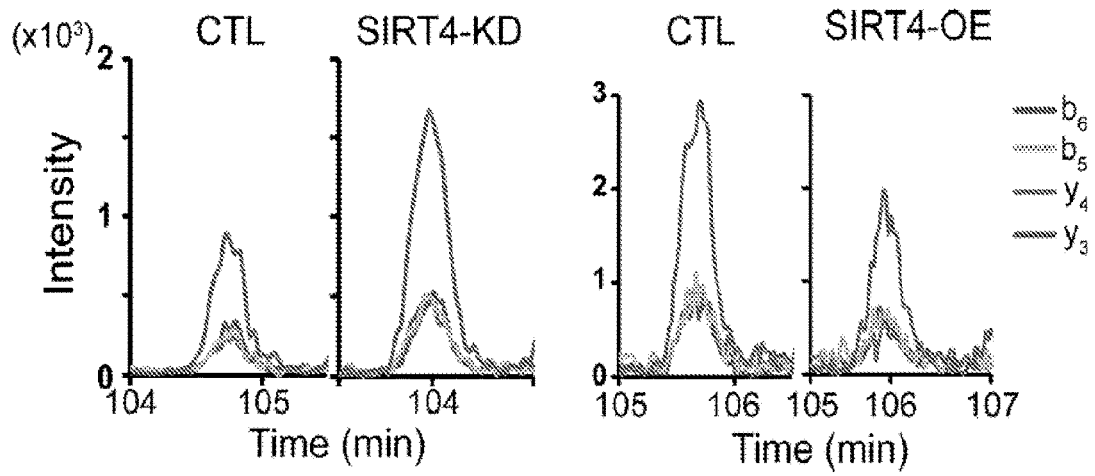
MS-based relative quantification of DLAT lipoyl-Lys in mitochondria
FIG. 6-1

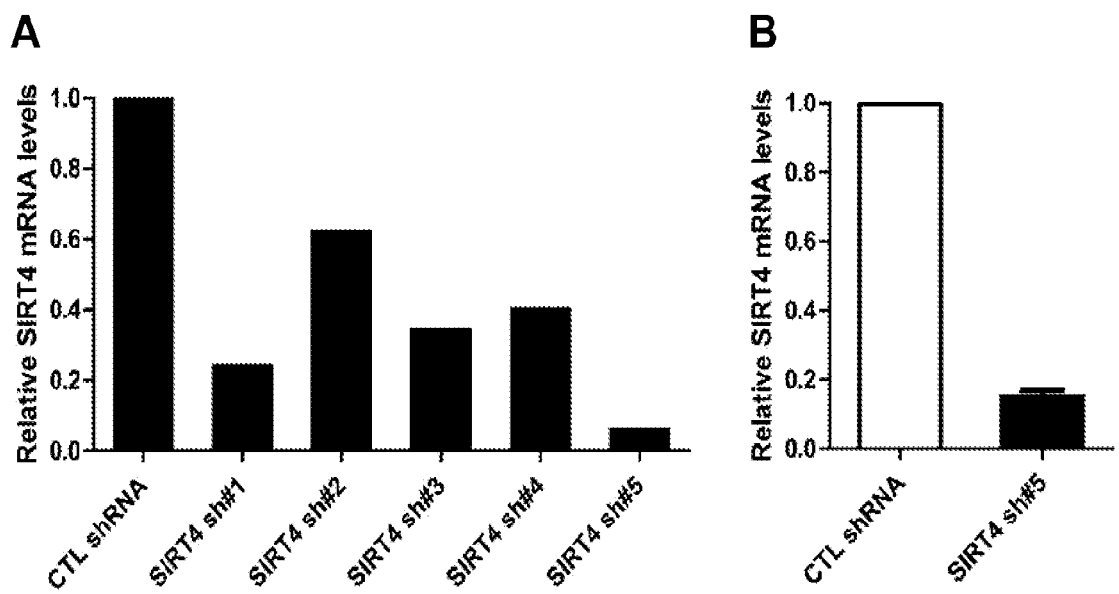
Generation of MRC5 cells with reduced SIRT4 expression
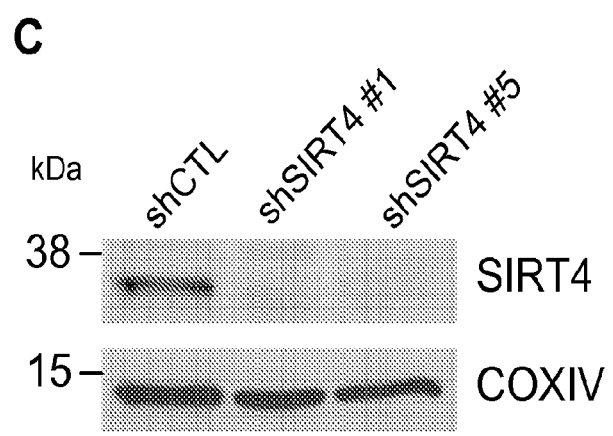
FIG. 7

SIRT4 interacting protein partners

| UniProt Accession | Gene | Description | Assigned Spectra EGFP IP | Assigned Spectra SIRT4-EGFP IP | Average SAINT Score |
|---|---|---|---|---|---|
| Q5JTZ9 | AARS2 | Alanine--tRNA ligase, mitochondrial (EC 6.1.1.7) (Alanyl-tRNA synthetase) (AlaRS) | 0\|0 | 9\|13 | 1 |
| Q9H845 | ACAD9 | Acyl-CoA dehydrogenase family member 9, mitochondrial (ACAD-9) (EC 1.3.99.-) | 0\|0 | 16\|20 | 1 |
| P49748 | ACADVL | Very long-chain specific acyl-CoA dehydrogenase, mitochondrial (VLCAD) (EC 1.3.8.9 | 8\|9 | 53\|75 | 0.96 |
| P24752 | ACAT1 | Acetyl-CoA acetyltransferase, mitochondrial (EC 2.3.1.9 ) (Acetoacetyl-CoA thiolase ) (T2 | 2\|0 | 31\|43 | 1 |
| Q9Y305 | ACOT9 | Acyl-coenzyme A thioesterase 9, mitochondrial (Acyl-CoA thioesterase 9) (EC 3.1.2.-) (Acyl-CoA thioester hydrolase 9) | 1\|0 | 11\|28 | 1 |
| Q96CM8 | ACSF2 | Acyl-CoA synthetase family member 2, mitochondrial (EC 6.2.1.-) | 0\|0 | 7\|3 | 0.96 |
| Q4G176 | ACSF3 | Acyl-CoA synthetase family member 3, mitochondrial (EC 6.2.1.-) | 0\|0 | 5\|4 | 0.98 |
| P13196 | ALAS1 | 5-aminolevulinate synthase, nonspecific, mitochondrial (ALAS-H) (EC 2.3.1.37) (5-aminolevulinic acid synthase 1) (Delta-ALA synthase 1) (Delta-aminolevulinate synthase 1) | 0\|0 | 3\|3 | 0.96 |
| P54886 | ALDH18A1 | Delta-1-pyrroline-5-carboxylate synthase (P5CS) (Aldehyde dehydrogenase family 18 member A1) [Includes: Glutamate 5-kinase (GK) (EC 2.7.2.11) (Gamma-glutamyl kinase); Gamma-glutamyl phosphate reductase (GPR) (EC 1.2.1.41) (Glutamate-5-semialdehyde dehydrogenase) (Glutamyl-gamma-semialdehyde dehydrogenase)] | 2\|0 | 24\|18 | 0.98 |
| O75891 | ALDH1L1 | Cytosolic 10-formyltetrahydrofolate dehydrogenase (10-FTHFDH) (FDH) (EC 1.5.1.6) (Aldehyde dehydrogenase family 1 member L1) | 0\|0 | 4\|4 | 0.98 |
| Q3SY69 | ALDH1L2 | Mitochondrial 10-formyltetrahydrofolate dehydrogenase (Mitochondrial 10-FTHFDH) (mtFDH) (EC 1.5.1.6) (Aldehyde dehydrogenase family 1 member L2) | 3\|2 | 41\|48 | 1 |
| P05091 | ALDH2 | Aldehyde dehydrogenase, mitochondrial (EC 1.2.1.3) (ALDH class 2) (ALDH-E2) (ALDHI) | 0\|1 | 14\|25 | 1 |
| P12694 | BCKDHA | 2-oxoisovalerate dehydrogenase subunit alpha, mitochondrial (EC 1.2.4.4) (Branched-chain alpha-keto acid dehydrogenase E1 component alpha chain) (BCKDE1A) (BCKDH E1-alpha) | 0\|0 | 3\|6 | 0.99 |
| Q9BSJ5 | C17orf80 | Uncharacterized protein C17orf80 (Cell migration-inducing gene 3 protein) (Human lung cancer oncogene 6 protein) (HLC-8) | 0\|0 | 5\|3 | 0.96 |
| Q9BXW7 | CECR5 | Cat eye syndrome critical region protein 5 | 0\|0 | 3\|7 | 0.99 |
| O76031 | CLPX | ATP-dependent Clp protease ATP-binding subunit clpX-like, mitochondria | 1\|0 | 13\|21 | 1 |
| P09543 | CNP | 2',3'-cyclic-nucleotide 3'-phosphodiesterase (CNP) (CNPase) (EC 3.1.4.37) | 0\|0 | 9\|16 | 1 |
| P36551 | CPOX | Coproporphyrinogen-III oxidase, mitochondrial (COX) (Coprogen oxidase) (Coproporphyrinogenase) (EC 1.3.3.3) | 0\|0 | 3\|3 | 0.96 |
| Q9UHQ9 | CYB5R1 | NADH-cytochrome b5 reductase 1 (b5R.1) (EC 1.6.2.2) (Humb5R2) (NAD(P)H:quinone oxidoreductase type 3 polypeptide A2) | 0\|0 | 5\|4 | 0.99 |
| P51398 | DAP3 | 28S ribosomal protein S29, mitochondrial (MRP-S29) (S29mt) (Death-associated protein 3) (DAP-3) (Ionizing radiation resistance conferring protein) | 0\|0 | 7\|5 | 1 |
| P11182 | DBT | Lipoamide acyltransferase component of branched-chain alpha-keto acid dehydrogenase complex, mitochondrial (EC 2.3.1.168) (Branched-chain alpha-keto acid dehydrogenase complex component E2) (BCKAD-E2) (BCKADE2) (Dihydrolipoamide acetyltransferase component of branched-chain alpha-keto acid dehydrogenase complex) (Dihydrolipoamide branched chain transacylase) (Dihydrolipoyllysine-residue (2-methylpropanoyl)transferase) | 0\|0 | 3\|6 | 0.96 |
| Q7L2E3 | DHX30 | Putative ATP-dependent RNA helicase DHX30 (EC 3.6.4.13 ) (DEAH box protein 30) | 0\|0 | 9\|21 | 1 |
| P10515 | DLAT | Dihydrolipoyllysine-residue acetyltransferase component of pyruvate dehydrogenase complex, mitochondrial (EC 2.3.1.12) (70 kDa mitochondrial autoantigen of primary biliary cirrhosis) (PBC) (Dihydrolipoamide acetyltransferase component of pyruvate dehydrogenase complex) (M2 antigen complex 70 kDa subunit) (Pyruvate dehydrogenase complex component E2) (PDC-E2) (PDCE2) | 0\|1 | 22\|22 | 1 |
| P09622 | DLD | Dihydrolipoyl dehydrogenase, mitochondrial (EC 1.8.4) (Dihydrolipoamide dehydrogenase) (Glycine cleavage system L protein) | 0\|0 | 8\|13 | 1 |
| P36957 | DLST | Dihydrolipoyllysine-residue succinyltransferase component of 2-oxoglutarate dehydrogenase complex, mitochondrial (EC 2.3.1.61) (2-oxoglutarate dehydrogenase complex component E2) (OGDC-E2) (Dihydrolipoamide succinyltransferase component of 2-oxoglutarate dehydrogenase complex) (E2K) | 0\|0 | 19\|26 | 1 |
| Q9ULA0 | DNPEP | Aspartyl aminopeptidase (EC 3.4.11.21) | 0\|0 | 11\|14 | 1 |
| Q13011 | ECH1 | Delta(3,5)-Delta(2,4)-dienoyl-CoA isomerase, mitochondrial (EC 5.3.3.-) | 0\|0 | 14\|14 | 1 |
| P30084 | ECHS1 | Enoyl-CoA hydratase, mitochondrial (EC 4.2.1.17) (Enoyl-CoA hydratase 1) (Short-chain enoyl-CoA hydratase) (SCEH) | 0\|0 | 4\|20 | 0.99 |
| P13804 | ETFA | Electron transfer flavoprotein subunit alpha, mitochondrial (Alpha-ETF) | 0\|0 | 5\|7 | 0.99 |
| O95571 | ETHE1 | Protein ETHE1, mitochondrial (EC 3.-.-.-) (Ethylmalonic encephalopathy protein 1) (Hepatoma subtracted clone one protein) | 0\|0 | 4\|10 | 0.99 |
| Q7L8L6 | FASTKD5 | FAST kinase domain-containing protein 5 | 0\|0 | 3\|4 | 0.97 |
| Q8NFF5 | FLAD1 | FAD synthase (EC 2.7.7.2) (FAD pyrophosphorylase) (FMN adenylyltransferase) (Flavin adenine dinucleotide synthase) [Includes: Molybdenum cofactor biosynthesis protein-like region; FAD synthase region] | 0\|0 | 6\|8 | 1 |
| P41250 | GARS | Glycine--tRNA ligase (EC 6.1.1.14) (Diadenosine tetraphosphate synthetase) (AP-4-A synthetase) (Glycyl tRNA synthetase) (GlyRS) | 0\|0 | 10\|9 | 1 |
| Q92947 | GCDH | Glutaryl-CoA dehydrogenase, mitochondrial (GCD) (EC 1.3.8.6) | 0\|0 | 4\|3 | 0.96 |
| P00367 | GLUD1 | Glutamate dehydrogenase 1, mitochondrial (GDH 1) (EC 1.4.1.3) | 0\|0 | 10\|14 | 1 |
| Q8TD30 | GPT2 | Alanine aminotransferase 2 (ALT2) (EC 2.6.1.2) (Glutamate pyruvate transaminase 2) (GPT 2) (Glutamic--alanine transaminase 2) (Glutamic--pyruvic transaminase 2) | 0\|0 | 8\|13 | 1 |
| P07203 | GPX1 | Glutathione peroxidase 1 (GPx-1) (GSHPx-1) (EC 1.11.1.9 ) (Cellular glutathione peroxidase | 0\|0 | 9\|14 | 1 |
| P40939 | HADHA | Trifunctional enzyme subunit alpha, mitochondrial (78 kDa gastrin-binding protein) (TP-alpha) [Includes: Long-chain enoyl-CoA hydratase (EC 4.2.1.17); Long chain 3-hydroxyacyl-CoA dehydrogenase (EC 1.1.1.211)] | 9\|7 | 54\|62 | 0.97 |
| Q9UBN7 | HDAC6 | Histone deacetylase 6 (HD6) (EC 3.5.1.98) | 0\|0 | 8\|4 | 0.98 |
| P35914 | HMGCL | Hydroxymethylglutaryl-CoA lyase, mitochondrial (HL) (HMG-CoA lyase) (EC 4.1.3.4) (3-hydroxy-3-methylglutarate-CoA lyase) | 0\|0 | 7\|6 | 1 |

| | | | | | |
|---|---|---|---|---|---|
| Q99714 | HSD17B10 | 3-hydroxyacyl-CoA dehydrogenase type-2 (EC 1.1.1.35) (17-beta-hydroxysteroid dehydrogenase 10) (17-beta-HSD 10) (3-hydroxy-2-methylbutyryl-CoA dehydrogenase) (EC 1.1.1.178) (3-hydroxyacyl-CoA dehydrogenase type II) (Endoplasmic reticulum-associated amyloid beta-peptide-binding protein) (Mitochondrial ribonuclease P protein 2) (Mitochondrial RNase P protein 2) (Short-chain type dehydrogenase/reductase XH98G2) (Type II HADH) | 1\|1 | 11\|30 | 1 |
| P10809 | HSPD1 | 60 kDa heat shock protein, mitochondrial (60 kDa chaperonin) (Chaperonin 60) (CPN60) (Heat shock protein 60) (HSP-60) (Hsp60) (HuCHA60) (Mitochondrial matrix protein P1) (P60 lymphocyte protein) | 8\|6 | 124\|142 | 1 |
| Q9NSE4 | IARS2 | Isoleucine--tRNA ligase, mitochondrial (EC 6.1.1.5 ) (Isoleucyl-tRNA synthetase) (IleRS) | 1\|0 | 14\|13 | 1 |
| Q5T440 | IBA57 | Putative transferase CAF17, mitochondrial (EC 2.1.-.-) (Iron-sulfur cluster assembly factor homolog) | 0\|0 | 6\|5 | 0.95 |
| P14735 | IDE | Insulin-degrading enzyme | 0\|3 | 34\|44 | 1 |
| P48735 | IDH2 | Isocitrate dehydrogenase [NADP], mitochondrial (IDH) (EC 1.1.1.42) (ICD-M) (IDP) (NADP(+)-specific ICDH) (Oxalosuccinate decarboxylase) | 0\|0 | 6\|9 | 1 |
| P26440 | IVD | Isovaleryl-CoA dehydrogenase, mitochondrial (IVD) (EC 1.3.8.4 ) | 0\|0 | 6\|8 | 0.99 |
| P36776 | LONP1 | Lon protease homolog, mitochondrial (EC 3.4.21.-) (LONHs) (Lon protease-like protein) (LONP) (Mitochondrial ATP-dependent protease Lon) (Serine protease 15 ) | 0\|0 | 16\|17 | 1 |
| P42704 | LRPPRC | Leucine-rich PPR motif-containing protein, mitochondrial (130 kDa leucine-rich protein) (LRP 130) (GP130) | 1\|0 | 13\|22 | 1 |
| Q96RQ3 | MCCC1 | Methylcrotonoyl-CoA carboxylase subunit alpha, mitochondrial (MCCase subunit alpha) (EC 6.4.1.4) (3-methylcrotonyl-CoA carboxylase 1) (3-methylcrotonyl-CoA carboxylase biotin-containing subunit) (3-methylcrotonyl-CoA:carbon dioxide ligase subunit alpha) | 0\|0 | 42\|56 | 1 |
| Q9HCC0 | MCCC2 | Methylcrotonoyl-CoA carboxylase beta chain, mitochondrial (MCCase subunit beta) (EC 6.4.1.4) (3-methylcrotonyl-CoA carboxylase 2) (3-methylcrotonyl-CoA carboxylase non-biotin-containing subunit) (3-methylcrotonyl-CoA:carbon dioxide ligase subunit beta) | 0\|0 | 83\|125 | 1 |
| P23368 | ME2 | NAD-dependent malic enzyme (NAD-ME ) (EC 1.1.1.38 ) (Malic enzyme 2) | 0\|0 | 4\|3 | 0.97 |
| Q99797 | MIPEP | Mitochondrial intermediate peptidase (MIP) (EC 3.4.24.59 ) | 1\|0 | 9\|13 | 0.99 |
| O95822 | MLYCD | Malonyl-CoA decarboxylase, mitochondrial (MCD) (EC 4.1.1.9 ) | 0\|0 | 3\|9 | 0.97 |
| Q8IVH4 | MMAA | Methylmalonic aciduria type A protein, mitochondrial (EC 3.6.-.-) | 0\|0 | 7\|5 | 0.98 |
| Q9BYD6 | MRPL1 | 39S ribosomal protein L1, mitochondrial (L1mt) (MRP-L1 ) | 0\|0 | 6\|7 | 0.98 |
| Q13084 | MRPL28 | 39S ribosomal protein L28, mitochondrial (L28mt) (MRP-L28) (Melanoma antigen p15) (Melanoma associated antigen recognized by T-lymphocytes) | 0\|0 | 3\|3 | 0.96 |
| Q9BZE1 | MRPL37 | 39S ribosomal protein L37, mitochondrial (L37mt) (MRP-L37) (39S ribosomal protein L2, mitochondrial) (L2mt) (MRP-L2 ) | 0\|1 | 10\|9 | 0.98 |
| Q96DV4 | MRPL38 | 39S ribosomal protein L38, mitochondrial (L38mt) (MRP-L38 ) | 0\|0 | 8\|13 | 1 |
| Q9NYK5 | MRPL39 | 39S ribosomal protein L39, mitochondrial (L39mt) (MRP-L39) (39S ribosomal protein L5, mitochondrial) (L5mt) (MRP-L5 ) | 0\|0 | 9\|6 | 1 |
| Q9H9J2 | MRPL44 | 39S ribosomal protein L44, mitochondrial (L44mt) (MRP-L44 ) (EC 3.1.26.-) | 0\|0 | 4\|4 | 0.98 |
| Q9Y676 | MRPS18B | 28S ribosomal protein S18b, mitochondrial (MRP-S18-b) (Mrps18-b) (S18mt-b) (28S ribosomal protein S18 2, mitochondrial) (MRP-S18-2 ) | 0\|0 | 3\|5 | 0.99 |
| P82650 | MRPS22 | 28S ribosomal protein S22, mitochondrial (MRP-S22 ) (S22mt) | 0\|0 | 14\|10 | 1 |
| Q9Y3D9 | MRPS23 | 28S ribosomal protein S23, mitochondrial (MRP-S23 ) (S23mt) | 0\|0 | 4\|9 | 0.99 |
| Q9NP92 | MRPS30 | 28S ribosomal protein S30, mitochondrial (MRP-S30) (S30mt) (Programmed cell death protein 9 ) | 0\|0 | 4\|6 | 0.96 |
| P82933 | MRPS9 | 28S ribosomal protein S9, mitochondrial (MRP-S9 ) (S9mt) | 0\|0 | 3\|6 | 0.98 |
| Q6UB35 | MTHFD1L | Monofunctional C1-tetrahydrofolate synthase, mitochondrial (EC 6.3.4.3) (Formyltetrahydrofolate synthetase) | 0\|1 | 12\|24 | 1 |
| Q4G0N4 | NADKD1 | NAD kinase domain-containing protein 1, mitochondrial (EC 2.7.1.23 ) | 0\|0 | 6\|11 | 0.99 |
| P28331 | NDUFS1 | NADH-ubiquinone oxidoreductase 75 kDa subunit, mitochondrial (EC 1.6.5.3) (EC 1.6.99.3) (Complex I 75kD ) (CI-75kD ) | 1\|1 | 30\|33 | 1 |
| O75306 | NDUFS2 | NADH dehydrogenase [ubiquinone] iron-sulfur protein 2, mitochondrial (EC 1.6.5.3) (EC 1.6.99.3) (Complex I-49kD) (CI-49kD) (NADH-ubiquinone oxidoreductase 49 kDa subunit) | 0\|0 | 8\|11 | 1 |
| P49821 | NDUFV1 | NADH dehydrogenase [ubiquinone] flavoprotein 1, mitochondrial (EC 1.6.5.3) (EC 1.6.99.3) (Complex I-51kD) (CI-51kD) (NADH dehydrogenase flavoprotein 1) (NADH-ubiquinone oxidoreductase 51 kDa subunit) | 0\|0 | 7\|13 | 0.99 |
| Q86X76 | NIT1 | Nitrilase homolog 1 (EC 3.5.-.-) | 0\|0 | 5\|4 | 0.96 |
| Q86UT6 | NLRX1 | NLR family member X1 (Caterpiller protein 11.3) (CLR11.3) (Nucleotide-binding oligomerization domain protein 26) (Nucleotide-binding oligomerization domain protein 5) (Nucleotide-binding oligomerization domain protein 9) | 0\|0 | 17\|14 | 1 |
| Q9H857 | NT5DC2 | 5'-nucleotidase domain-containing protein 2 (EC 3.1.3.-) | 0\|0 | 23\|30 | 1 |
| Q86UY8 | NT5DC3 | 5'-nucleotidase domain-containing protein 3 (EC 3.1.3.-) (GRP94-neighboring nucleotidase) | 0\|0 | 3\|5 | 0.97 |
| Q02218 | OGDH | 2-oxoglutarate dehydrogenase, mitochondrial (EC 1.2.4.2) (2-oxoglutarate dehydrogenase complex component E1) (OGDC-E1 ) (Alpha-ketoglutarate dehydrogenase) | 1\|0 | 13\|14 | 1 |
| P11498 | PC | Pyruvate carboxylase, mitochondrial (EC 6.4.1.1 ) (Pyruvic carboxylase) (PCB) | 0\|0 | 9\|14 | 1 |
| P05165 | PCCA | Propionyl-CoA carboxylase alpha chain, mitochondrial (PCCase subunit alpha) (EC 6.4.1.3) (Propanoyl-CoA:carbon dioxide ligase subunit alpha) | 0\|0 | 9\|12 | 1 |
| Q16822 | PCK2 | Phosphoenolpyruvate carboxykinase [GTP], mitochondrial (PEPCK-M) (EC 4.1.1.32) (Phosphoenolpyruvate carboxylase) | 0\|0 | 6\|6 | 1 |
| Q6L8Q7 | PDE12 | 2',5'-phosphodiesterase 12 (2'-PDE) (2-PDE) (EC 3.1.4.-) | 0\|0 | 8\|5 | 0.99 |
| P11177 | PDHB | Pyruvate dehydrogenase E1 component subunit beta, mitochondrial (PDHE1-B) (EC 1.2.4.1 ) | 0\|0 | 11\|10 | 1 |
| O00330 | PDHX | Pyruvate dehydrogenase protein X component, mitochondrial (Dihydrolipoamide dehydrogenase-binding protein of pyruvate dehydrogenase complex) (E3-binding protein) (E3BP) (Lipoyl-containing pyruvate dehydrogenase complex component X) (proX) | 0\|0 | 9\|17 | 1 |
| Q9P0J1 | PDP1 | [Pyruvate dehydrogenase [acetyl-transferring]]-phosphatase 1, mitochondrial (PDP 1) (EC 3.1.3.43) (Protein phosphatase 2C) (Pyruvate dehydrogenase phosphatase catalytic subunit 1) (PDPC 1) | 0\|0 | 3\|4 | 0.97 |
| Q5JRX3 | PITRM1 | Presequence protease, mitochondrial (hPreP) (EC 3.4.24.-) (Pitrilysin metalloproteinase 1) (Metalloprotease 1) (hMP1) | 0\|0 | 5\|12 | 1 |
| Q10713 | PMPCA | Mitochondrial-processing peptidase subunit alpha (EC 3.4.24.64 ) (Alpha-MPP ) (P-55) | 0\|0 | 3\|15 | 0.96 |
| O75439 | PMPCB | Mitochondrial-processing peptidase subunit beta (EC 3.4.24.64 ) (Beta-MPP ) (P-52) | 0\|0 | 8\|16 | 1 |

2 of 3

| | | | | | |
|---|---|---|---|---|---|
| Q9H2U2 | PPA2 | Inorganic pyrophosphatase 2, mitochondrial (EC 3.6.1.1) (Pyrophosphatase SID6-306) (Pyrophosphate phospho-hydrolase 2) (PPase 2) | 1\|0 | 8\|7 | 0.96 |
| P30048 | PRDX3 | Thioredoxin-dependent peroxide reductase, mitochondrial (EC 1.11.1.15) (Antioxidant protein 1) (AOP-1) (HBC189) (Peroxiredoxin III) (Prx-III) (Peroxiredoxin-3) (Protein MER5 homolog) | 3\|2 | 19\|30 | 0.98 |
| P30044 | PRDX5 | Peroxiredoxin-5, mitochondrial (EC 1.11.1.15) (Alu corepressor 1) (Antioxidant enzyme B166) (AOEB166) (Liver tissue 2D-page spot 71B) (PLP) (Peroxiredoxin V) (Prx-V) (Peroxisomal antioxidant enzyme) (TPx type VI) (Thioredoxin peroxidase PMP20) (Thioredoxin reductase) | 0\|0 | 8\|15 | 1 |
| Q96EY7 | PTCD3 | Pentatricopeptide repeat domain-containing protein 3, mitochondrial (Transformation-related gene 15 protein) (TRG-15) | 0\|0 | 4\|7 | 0.99 |
| P32322 | PYCR1 | Pyrroline-5-carboxylate reductase 1, mitochondrial (P5C reductase 1) (P5CR 1) (EC 1.5.1.2) | 0\|0 | 13\|11 | 1 |
| Q96C36 | PYCR2 | Pyrroline-5-carboxylate reductase 2 (P5C reductase 2) (P5CR 2) (EC 1.5.1.2) | 1\|1 | 13\|17 | 0.99 |
| Q5T160 | RARS2 | Probable arginine-tRNA ligase, mitochondrial (EC 6.1.1.19) (Arginyl-tRNA synthetase) (ArgRS) | 2\|1 | 17\|23 | 1 |
| Q9NP81 | SARS2 | Serine--tRNA ligase, mitochondrial (EC 6.1.1.11) (SerRSmt) (Seryl-tRNA synthetase) (SerRS) (Seryl tRNA (Ser/Sec) synthetase) | 0\|0 | 7\|13 | 1 |
| P29353 | SHC1 | SHC-transforming protein 1 (SHC-transforming protein 3) (SHC-transforming protein A) (Src homology 2 domain-containing-transforming protein C1) (SH2 domain protein C1) | 0\|0 | 6\|4 | 0.95 |
| P34897 | SHMT2 | Serine hydroxymethyltransferase, mitochondrial (SHMT) (EC 2.1.2.1) (Glycine hydroxymethyltransferase) (Serine methylase) | 0\|0 | 5\|6 | 0.99 |
| Q9Y6E7 | SIRT4 | NAD-dependent protein deacetylase sirtuin-4 (EC 3.5.1.-) (NAD-dependent ADP-ribosyltransferase sirtuin-4 (EC 2.4.2.-) (Regulatory protein SIR2 homolog 4) (SIR2-like protein 4) | 0\|0 | 57\|70 | 1 |
| Q9UJZ1 | STOML2 | Stomatin-like protein 2, mitochondrial (SLP-2) (EPB72-like protein 2) (Paraprotein target 7) (Paratarg-7) | 1\|1 | 20\|18 | 1 |
| Q9P2R7 | SUCLA2 | Succinyl-CoA ligase [ADP-forming] subunit beta, mitochondrial (EC 6.2.1.5) (ATP-specific succinyl-CoA synthetase subunit beta) (Renal carcinoma antigen NY-REN-39) (Succinyl-CoA synthetase beta-A chain) (SCS-betaA) | 0\|0 | 2\|5 | 0.95 |
| Q96I99 | SUCLG2 | Succinyl-CoA ligase [GDP-forming] subunit beta, mitochondrial (EC 6.2.1.4) (GTP-specific succinyl-CoA synthetase subunit beta) (Succinyl-CoA synthetase beta-G chain) (SCS-betaG) | 1\|0 | 5\|9 | 0.96 |
| Q969Z0 | TBRG4 | Protein TBRG4 (Cell cycle progression restoration protein 2) (Cell cycle progression protein 2) (FAST kinase domain-containing protein 4) (Transforming growth factor beta regulator 4) | 0\|0 | 3\|3 | 0.98 |
| Q8IYQ7 | THNSL1 | Threonine synthase-like 1 (TSH1) | 0\|0 | 4\|6 | 0.99 |
| O96008 | TOMM40 | Mitochondrial import receptor subunit TOM40 homolog (Protein Haymaker) (Translocase of outer membrane 40 kDa subunit homolog) (p38.5) | 0\|0 | 7\|7 | 1 |
| Q12931 | TRAP1 | Heat shock protein 75 kDa, mitochondrial (HSP 75) (TNFR-associated protein 1) (Tumor necrosis factor type 1 receptor-associated protein) (TRAP-1) | 0\|0 | 13\|12 | 1 |
| P49411 | TUFM | Elongation factor Tu, mitochondrial (EF-Tu) (P43) | 8\|6 | 68\|98 | 1 |
| A3KMH1 | VWA8 | von Willebrand factor A domain-containing protein 8 | 3\|1 | 25\|28 | 0.99 |

FIG. 9 continued

Synthetic acyl-peptides

| Peptide | Sequence | |
|---|---|---|
| H3K9-Lipoyl | KQTARK[Lipoyl]STGGWW | SEQ ID NO: 3 |
| H3K9-Biotin | KQTARK[Biotin]STGGWW | SEQ IDNO: 4 |
| H3K9-Acetyl | KQTARK[Acetyl]STGGWW | SEQ IDNO: 5 |
| H3K9 | KQTARKSTGGWW | SEQ IDNO: 6 |
| DLAT-Lipoyl | TDK[Lipoyl]ATIGFE | SEQ IDNO: 7 |
| DLAT-Lipoyl | EIETDK[Lipoyl]ATIGWW | SEQ ID NO: 8 |
| DLAT-Lipoyl | EIETDK[Lipoyl]ATIGW | SEQ ID NO: 9 |
| DLAT-Acetyl | EIETDK[Acetyl]ATIGW | SEQ ID NO: 10 |
| DLAT | EIETDKATIGWW | SEQ ID NO: 11 |
| PDHX-Lipoyl | EIETDK[Lipoyl]AVVTWW | SEQ ID NO: 12 |
| PDHX | EIETDKAVVTWW | SEQ ID NO: 13 |

FIG. 10 shRNA sequences for RNA interference

| Mission shRNA | TRC #/product number | Sequence |
|---|---|---|
| shSIRT4 #1 | TRCN0000018944 | CCGGCCCGATTGCAATACTGAACATCTCGAGATGTTCAGTATTGCAATCGGGTTTTT SEQ ID NO:14 |
| shSIRT4 #2 | TRCN0000018945 | CCGGCCGTGCTCGAAAGCCTCCATTCTCGAGAATGGAGGCTTTCGAGCACGGTTTTT SEQ ID NO: 15 |
| shSIRT4 #3 | TRCN0000232894 | CCGGCTCCTGATGGTGACGTCTTTCCTCGAGGAAAGACGTCACCATCAGGAGTTTTTG SEQ ID NO: 16 |
| shSIRT4 #4 | TRCN0000232895 | CCGGGAACCCTGACAAGGTTGATTTCTCGAGAAATCAACCTTGTCAGGGTTCTTTTTG SEQ ID NO: 17 |
| shSIRT4 #5 | TRCN0000232898 | CCGGACAGGGACTTTCACTTGAATCCTCGAGGATTCAAGTGAAAGTCCCTGTTTTTG SEQ ID NO: 18 |
| shRNA control #1 | SHC016 | |
| shRNA control #2 | SHC202 | |

FIG. 11

Primers used for qRT-PCR

| Gene | Forward primer sequence | Reverse primer sequence |
|---|---|---|
| SIRT4 (for cloning into pLXSN) | AAACTCGAGATGAAGATGAGCTTTGCGTTG SEQ ID NO: 19 | AAAGGATCCGCATGGGTCTATCAAAGGCA SEQ ID NO: 20 |
| SIRT4 (for H161Y mutant generation) | GCCTGACAGAGCTCTACGGATGCATGGAC SEQ ID NO: 21 | GTCCATGCATCCGTAGAGCTCTGTCAGGC SEQ ID NO: 22 |
| SIRT4 (qRT-PCR) | CTTGGAAACGCTCTTGCAGCAC SEQ ID NO: 23 | CTTGGAAACGCTCTTGCAGCAC SEQ ID NO: 24 |
| GAPDH (qRT-PCR) | CGACAGTCAGCCGCATCTTCTTT SEQ ID NO: 25 | GGCAACAATATCCACTTTACCAGAG SEQ ID NO: 26 |
| Actin (qRT-PCR) | TCCTCCTGAGGGCAAGTACTC SEQ ID NO: 27 | CGGACTCGTCATACTCCTGCTT SEQ ID NO: 28 |

FIG. 12

A SIRT4 $k_{cat}/K_m$ estimation for acetyl substrates

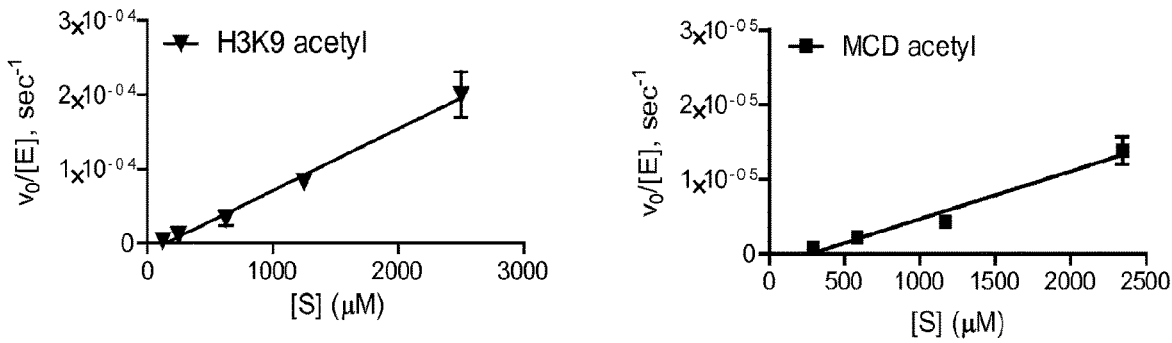

B $k_{cat}/K_m$ estimation for DLAT K259 acetyl

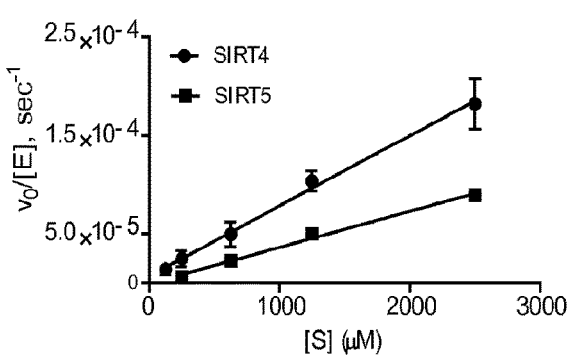

C BH plot for DLAT K259 lipoyl

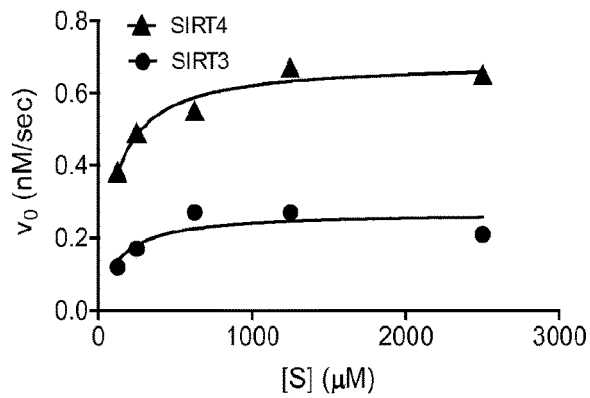

D SIRT3 BH plot for DLAT K259 acetyl

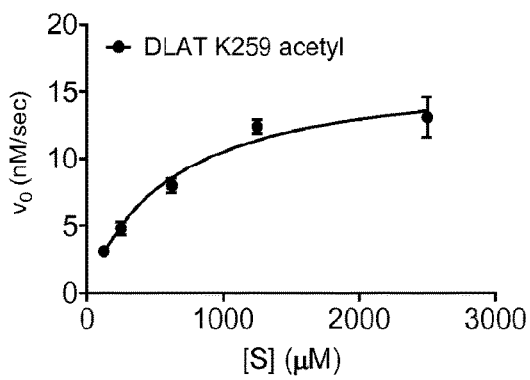

E Summary of SIRT kinetic parameters

| Peptide substrate Enzyme (0.5 μM) | $k_{cat}$ (s$^{-1}$) | $K_m$ (μM) | $k_{cat}/K_m$ (s$^{-1}$M$^{-1}$) |
|---|---|---|---|
| *SIRT3* | | | |
| DLAT K259 Acetyl | 0.034 ± 0.002 | 599 ± 141 | 56.1 ± 9.1 |
| DLAT K259 Lipoyl | 0.00054 ± 0.00007 | 124 ± 80 | 4.3 ± 2.4 |
| *SIRT4* | | | |
| DLAT K259 Acetyl | ND* | ND* (>2500) | 0.071 ± 0.007 |
| DLAT K259 Lipoyl | 0.0014 ± 0.0001 | 104 ± 20 | 13.2 ± 2.3 |
| *SIRT5* | | | |
| DLAT K259 Acetyl | ND* | ND* (>2500) | 0.037 ± 0.002 |
| DLAT K259 Lipoyl | - | - | - |

FIG. 13

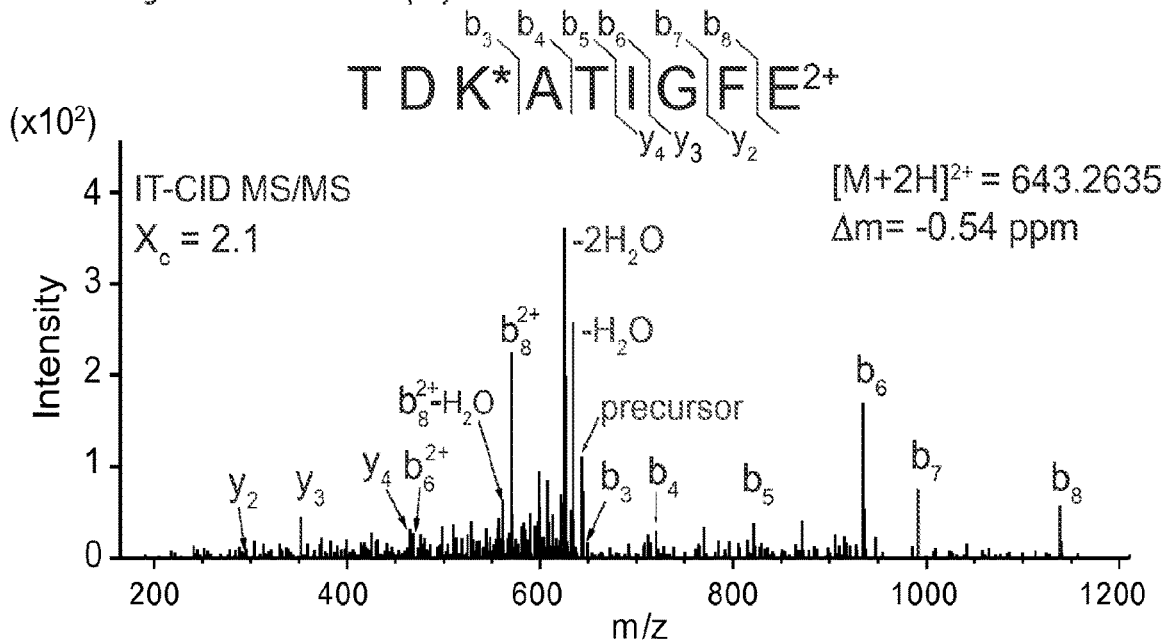
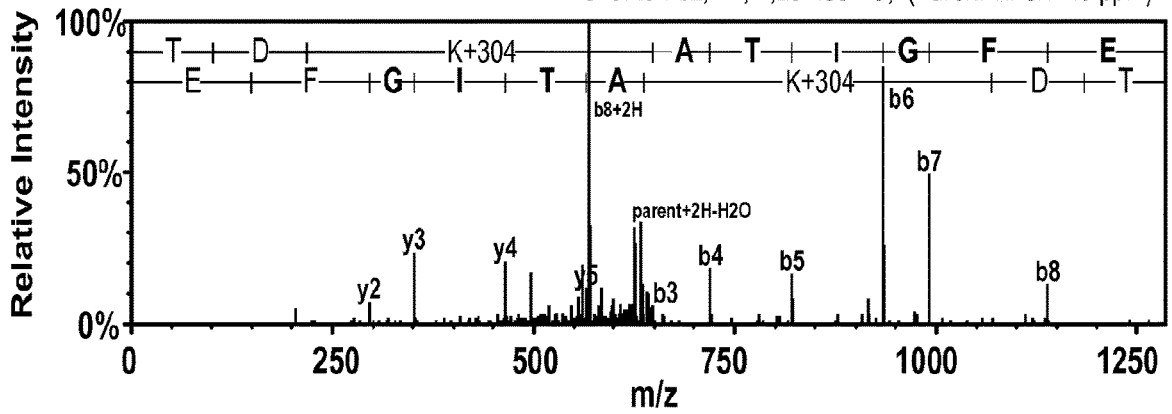
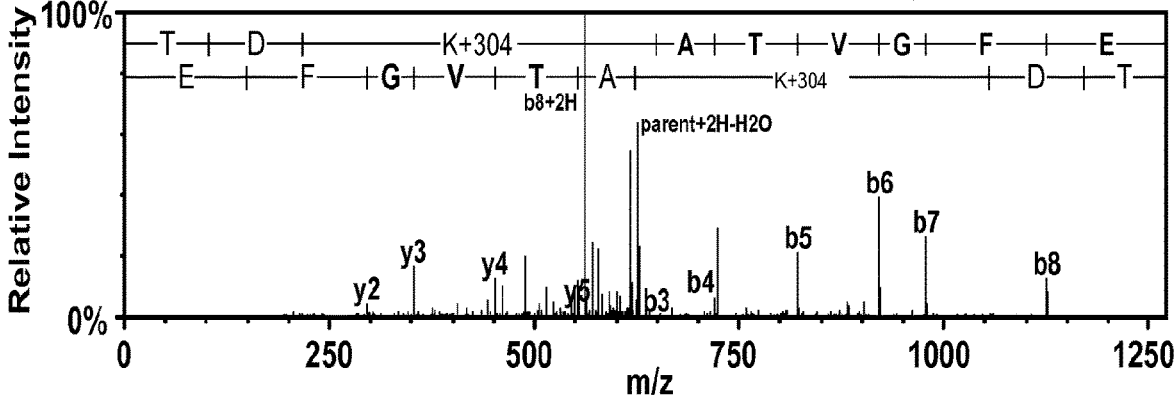
FIG. 15

SEQUENCE LISTING

<160> NUMBER OF SEQ ID NOS: 28

<210> SEQ ID NO 1
<211> LENGTH: 1213
<212> TYPE: DNA
<213> ORGANISM: Homo sapiens

<400> SEQUENCE: 1

```
gcaaatgcaa tcagacggtc ccactgtggg gtgtgaagtg tccgtagagc tgtgagagaa      60
tgaagatgag ctttgcgttg actttcaggt cagcaaaagg ccgttggatc gcaaacccca     120
gccagccgtg ctcgaaagcc tccattgggt tatttgtgcc agcaagtcct cctctggacc     180
ctgagaaggt caaagagtta cagcgcttca tcacccttc caagagactc cttgtgatga     240
ctggggcagg aatctccacc gaatcgggga taccagacta caggtcagaa aaagtggggc     300
tttatgcccg cactgaccgc aggcccatcc agcatggtga ttttgtccgg agtgcccaa      360 tccgccagcg gtactgggcg agaaacttcg taggctggcc tcaattctcc tcccaccagc     420
ctaaccctgc acactgggct ttgagcacct gggagaaact cggaaagctg tactggttgg     480
tgacccaaaa tgtggatgct ttgcacacca aggcggggag tcggcgcctg acagagctcc     540
acggatgcat ggacagggtc ctgtgcttgg attgtgggga acagactccc cgggggtgc      600 tgcaagagcg tttccaagtc ctgaacccca cctggagtgc tgaggcccat ggcctggctc     660
ctgatggtga cgtctttctc tcagaggagc aagtccggag ctttcaggtc ccaacctgcg     720
ttcaatgtgg aggccatctg aaaccagatg tcgttttctt cggggacaca gtgaaccctg     780
acaaggttga ttttgtgcac aagcgtgtaa aagaagccga ctccctcttg gtggtgggat     840
catccttgca ggtatactct ggttacaggt ttatcctcac tgcctgggag aagaagctcc     900
cgattgcaat actgaacatt gggcccacac ggtcggatga cttggcgtgt ctgaaactga     960
attctcgttg tggagagttg ctgcctttga tagacccatg ctgaccacag cctgatattc    1020
cagaacctgg aacagggact ttcacttgaa tcttgctgct aaatgtaaat gccttctcaa    1080
atgacagatt ccagttccca ttcaacagag tagggtgcac tgacaaagta tagaaggttc    1140
taggtatctt aatgtgtgga tattcttaat taaaactcat ttttttaaa taaaaattg     1200 ttcagcttta aaa                                                       1213
```

<210> SEQ ID NO 2
<211> LENGTH: 314
<212> TYPE: PRT
<213> ORGANISM: Homo sapiens

<400> SEQUENCE: 2

```
Met Lys Met Ser Phe Ala Leu Thr Phe Arg Ser Ala Lys Gly Arg Trp
1               5                   10                  15

Ile Ala Asn Pro Ser Gln Pro Cys Ser Lys Ala Ser Ile Gly Leu Phe
            20                  25                  30
```

```
Val Pro Ala Ser Pro Pro Leu Asp Pro Glu Lys Val Lys Glu Leu Gln
            35                  40                  45

Arg Phe Ile Thr Leu Ser Lys Arg Leu Leu Val Met Thr Gly Ala Gly
 50                  55                  60

Ile Ser Thr Glu Ser Gly Ile Pro Asp Tyr Arg Ser Glu Lys Val Gly
 65                  70                  75                  80

Leu Tyr Ala Arg Thr Asp Arg Arg Pro Ile Gln His Gly Asp Phe Val
                85                  90                  95

Arg Ser Ala Pro Ile Arg Gln Arg Tyr Trp Ala Arg Asn Phe Val Gly
            100                 105                 110

Trp Pro Gln Phe Ser Ser His Gln Pro Asn Pro Ala His Trp Ala Leu
            115                 120                 125

Ser Thr Trp Glu Lys Leu Gly Lys Leu Tyr Trp Leu Val Thr Gln Asn
130                 135                 140

Val Asp Ala Leu His Thr Lys Ala Gly Ser Arg Arg Leu Thr Glu Leu
145                 150                 155                 160

His Gly Cys Met Asp Arg Val Leu Cys Leu Asp Cys Gly Glu Gln Thr
                165                 170                 175

Pro Arg Gly Val Leu Gln Glu Arg Phe Gln Val Leu Asn Pro Thr Trp
            180                 185                 190

Ser Ala Glu Ala His Gly Leu Ala Pro Asp Gly Asp Val Phe Leu Ser
            195                 200                 205

Glu Glu Gln Val Arg Ser Phe Gln Val Pro Thr Cys Val Gln Cys Gly
            210                 215                 220

Gly His Leu Lys Pro Asp Val Val Phe Phe Gly Asp Thr Val Asn Pro
225                 230                 235                 240

Asp Lys Val Asp Phe Val His Lys Arg Val Lys Glu Ala Asp Ser Leu
                245                 250                 255

Leu Val Val Gly Ser Ser Leu Gln Val Tyr Ser Gly Tyr Arg Phe Ile
            260                 265                 270

Leu Thr Ala Trp Glu Lys Lys Leu Pro Ile Ala Ile Leu Asn Ile Gly
            275                 280                 285

Pro Thr Arg Ser Asp Asp Leu Ala Cys Leu Lys Leu Asn Ser Arg Cys
            290                 295                 300

Gly Glu Leu Leu Pro Leu Ile Asp Pro Cys
305                 310

<210> SEQ ID NO 3
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Lipoyl

<400> SEQUENCE: 3

Lys Gln Thr Ala Arg Lys Ser Thr Gly Gly Trp Trp
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Polypeptide
```

-continued

```
<220> FEATURE:
<221> NAME/KEY: MISC_FEATURE
<222> LOCATION: (6)..(6)
<223> OTHER INFORMATION: Biotin

<400> SEQUENCE: 4

Lys Gln Thr Ala Arg Lys Ser Thr Gly Gly Trp Trp
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Acetyl

<400> SEQUENCE: 5

Lys Gln Thr Ala Arg Lys Ser Thr Gly Gly Trp Trp
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 6

Lys Gln Thr Ala Arg Lys Ser Thr Gly Gly Trp Trp
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Lipoyl

<400> SEQUENCE: 7

Thr Asp Lys Ala Thr Ile Gly Phe Glu
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Lipoyl

<400> SEQUENCE: 8

Glu Ile Glu Thr Asp Lys Ala Thr Ile Gly Trp Trp
1               5                   10

<210> SEQ ID NO 9
<211> LENGTH: 11
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Lipoyl

<400> SEQUENCE: 9

Glu Ile Glu Thr Asp Lys Ala Thr Ile Gly Trp
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Acetyl

<400> SEQUENCE: 10

Glu Ile Glu Thr Asp Lys Ala Thr Ile Gly Trp
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 11

Glu Ile Glu Thr Asp Lys Ala Thr Ile Gly Trp Trp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Lipoyl

<400> SEQUENCE: 12

Glu Ile Glu Thr Asp Lys Ala Val Val Thr Trp Trp
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 13

Glu Ile Glu Thr Asp Lys Ala Val Val Thr Trp Trp
1               5                   10

<210> SEQ ID NO 14
<211> LENGTH: 57
<212> TYPE: DNA
<213> ORGANISM: Artificial Sequence
<220> FEATURE:
<223> OTHER INFORMATION: Synthetic Polynucleotide
```

<400> SEQUENCE: 14
ccggcccgat tgcaatactg aacatctcga gatgttcagt attgcaatcg ggttttt    57

<210> SEQ ID NO 15
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 15
ccggccgtgc tcgaaagcct ccattctcga gaatggaggc tttcgagcac ggttttt    57

<210> SEQ ID NO 16
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 16
ccggctcctg atggtgacgt ctttcctcga ggaaagacgt caccatcagg agttttg    58

<210> SEQ ID NO 17
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 17
ccgggaaccc tgacaaggtt gatttctcga gaaatcaacc ttgtcagggt tcttttg    58

<210> SEQ ID NO 18
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 18
ccggacaggg actttcactt gaatcctcga ggattcaagt gaaagtccct gttttttg   58

<210> SEQ ID NO 19
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 19
aaactcgaga tgaagatgag ctttgcgttg                                   30

<210> SEQ ID NO 20
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 20
aaaggatccg catgggtcta tcaaaggca                                    29

<210> SEQ ID NO 21

```
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 21
gcctgacaga gctctacgga tgcatggac                                      29

<210> SEQ ID NO 22
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 22
gtccatgcat ccgtagagct ctgtcaggc                                      29

<210> SEQ ID NO 23
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 23
cttggaaacg ctcttgcagc ac                                             22

<210> SEQ ID NO 24
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 24
cttggaaacg ctcttgcagc ac                                             22

<210> SEQ ID NO 25
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 25
cgacagtcag ccgcatcttc ttt                                            23

<210> SEQ ID NO 26
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 26
ggcaacaata tccactttac cagag                                          25

<210> SEQ ID NO 27
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 27
```

```
tcctcctgag ggcaagtact c                                              21

<210> SEQ ID NO 28
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 28
cggactcgtc atactcctgc tt                                             22
```

SIRT4 LIPOAMIDASE ACTIVITY AND USES THEREOF

STATEMENT OF U.S. GOVERNMENT INTEREST

This invention was made with government support under Grant Nos. DA026192, AI102187, AI078063, HD073044 and CA082396 awarded by the National Institutes of Health. The government has certain rights in the invention.

INCORPORATION BY REFERENCE OF MATERIAL SUBMITTED ELECTRONICALLY

This application contains, as a separate part of disclosure, a sequence listing in computer-readable form (filename: 48274_SubSeqListing.txt; 10, 674 bytes; created May 22, 2018) which is incorporated by reference in its entirety.

BACKGROUND

Sirtuins (SIRTs) are a family of seven mammalian nicotinamide adenine dinucleotide (NAD)-dependent enzymes that govern genome regulation, stress response, metabolic homeostasis and lifespan[1]. SIRTs contain conserved deacetylase domains[2], yet SIRTs4-7 show little to no deacetylase activity. Emerging evidence has revealed that, compared to acetylation, certain SIRTs favor hydrolysis of lysine fatty acid acylation (SIRT6)[3], succinylation, or malonylation (SIRT5)[4,5].

Mitochondrial SIRTs3-5 regulate ATP production, apoptosis, and cell signalling[9] through distinct enzymatic activities. SIRT3 is considered to be the major mitochondrial deacetylase[10], while SIRT5 efficiently desuccinylates and demalonylates proteins[4,5]. Although recently shown to regulate glutamine metabolism[11,12], SIRT4 enzymatic functions have generally remained elusive[13]. SIRT4 has been shown to ADP-ribosylate glutamate dehydrogenase (GLUD1) and regulate amino acid-dependent insulin secretion[6]. However, robust SIRT4 enzymatic activity has not been characterized, and knowledge of SIRT4 biological substrates and the cellular pathways it regulates remains limited. Initial studies reported limited deacetylation activity[14,15], yet SIRT4 has been shown to control lipid catabolism through deacetylation of malonyl-CoA decarboxylase (MCD)[16]. Additional SIRT4 acetyl-substrate candidates have been identified in vitro via human peptide microarrays[17]. Moreover, in vitro substrate specificities have been profiled using recombinant SIRTs and various acyl-histone peptides[18]. Despite increasing putative SIRT4 candidate substrates, reconciliation of in vitro enzymatic activities and in vivo biological substrates remains challenging.

SUMMARY

The present application is based on the discovery that SIRT4 acts as a cellular lipoamidase that regulates pyruvate dehydrogenase complex (PDHC) activity through hydrolysis of its lipoamide cofactors (e.g., dihydrolipoyllysine acetyltransferase (DLAT)).

In one aspect, described herein is a method of assaying lipoamidase activity of SIRT4 in a mammalian cell that expresses a SIRT4 polypeptide comprising measuring a level of a dihydrolipoyllysine acetyltransferase (DLAT) lipoamide in a cell that expresses a SIRT4 polypeptide, thereby assaying the lipoamidase activity of SIRT4 in the cell. In some embodiments, the cell comprises a decreased level of a DLAT lipoamide compared to a cell of the same type that does not express a SIRT4 polypeptide. In some embodiments, the DLAT lipoamide is selected from the group consisting of DLAT lipoyl-K259 (SEQ ID NO: 8) and DLAT lipoyl-K132 (SEQ ID NO 7).

In another aspect, described herein is a method of assaying lipoamidase activity of SIRT4 in a tissue sample, wherein the tissue sample comprises a cell that expresses a SIRT4 polypeptide, the method comprising measuring a level of a dihydrolipoyllysine acetyltransferase (DLAT) lipoamide in the tissue sample, thereby assaying the lipoamidase activity of SIRT4 in the cell. Exemplary tissue samples include, but are not limited to, liver tissue, heart tissue, brain tissue and kidney tissue. In some embodiments, the tissue sample comprises a decreased level of a DLAT lipoamide compared to a tissue of the same type that does not express a SIRT4 polypeptide. In some embodiments, the DLAT lipoamide is selected from the group consisting of DLAT lipoyl-K259 (SEQ ID NO: 8) and DLAT lipoyl-K132 (SEQ ID NO 7).

In another aspect, described herein is a method of modulating dihydrolipoyllysine acetyltransferase (DLAT) activity in a mammalian cell comprising contacting the cell with an agent that modulates the lipoamidase activity of a SIRT4 polypeptide, thereby modulating the DLAT activity in the mammalian cell. In some embodiments, the agent decreases the lipoamidase activity of the SIRT4 polypeptide, thereby increasing the DLAT activity in the mammalian cell. In some embodiments, the agent increases the lipoamidase activity of the SIRT4 polypeptide, thereby decreasing the DLAT activity in the mammalian cell. In some embodiments, the agent that modulates the lipoamidase activity of the SIRT4 polypeptide is selected from the group consisting of an antibody, a small molecule and an antisense oligonucleotide.

In some embodiments, measuring the lipoamidase activity of the SIRT4 polypeptide comprises measuring a level of a DLAT lipoamide in a cell that expresses a SIRT4 polypeptide. In some embodiments, the DLAT lipoamide is selected from the group consisting of DLAT lipoyl-K259 (SEQ ID NO: 8) and DLAT lipoyl-K132 (SEQ ID NO: 7).

In another aspect, described herein is a method of increasing pyruvate dehydrogenase complex (PDHC) activity in a mammalian cell comprising contacting the cell with an inhibitor of SIRT4 lipoamidase activity, thereby increasing PDHC activity in the cell. In some embodiments, the cell is contacted with the inhibitor in an amount effective to increase a level of dihydrolipoyllysine acetyltransferase (DLAT) lipoamide in the cell compared to a cell of the same type that is not contacted with the inhibitor.

In another aspect, described herein is a method for identifying a candidate agent that increases dihydrolipoyllysine acetyltransferase (DLAT) activity in a cell that expresses a SIRT4 polypeptide, the method comprising contacting the cell with the candidate agent; and measuring SIRT4 lipoamidase activity in the cell, wherein a decreased level of SIRT4 lipoamidase activity in the cell relative to a predetermined criterion identifies the agent as an agent that increases DLAT activity in the cell. In some embodiments, the candidate agent is selected from the group consisting of an antibody, a small molecule and an antisense oligonucleotide. The term "predetermined criterion" as used herein refers to a level of lipoamidase activity (or dihydrolipoyllysine acetyltransferase (DLAT) activity) in a cell that does not express a SIRT4 polypeptide (i.e., a control sample). In some embodiments, the predetermined criterion includes information such as mean, standard deviation, quartile measurements, confidence intervals, or other information about the lipoamidase activity of SIRT4 (or dihydrolipoyllysine acetyltransferase (DLAT) activity) in the cell. In still other variations, the predetermined criterion is a receiver operating characteristic curve based on data of lipoamidase activity (or dihydrolipoyllysine acetyltransferase (DLAT) activity) measurements in subjects with a metabolic disorder and subjects that do not have a metabolic disorder. Optionally, the predetermined criterion is based on subjects further stratified by other characteristics that can be determined for a subject, to further refine the diagnostic precision. Such additional characteristics include, for example, sex, age, weight, smoking habits, race or ethnicity, blood pressure, other diseases, and medications.

In some embodiments, the method comprises measuring SIRT4 lipoamidase activity comprises measuring a level of a dihydrolipoyllysine acetyltransferase (DLAT) lipoamide, such as DLAT lipoyl-K259 (SEQ ID NO: 8) and DLAT lipoyl-K132 (SEQ ID NO: 7), in the cell. An increased level of a DLAT lipoamide in the cell is indicative of a decreased level of SIRT4 lipoamidase activity in the cell.

In any of the methods described herein, in some embodiments, the cell expresses an endogenous SIRT4 polypeptide. In other embodiments, the cell is engineered to express a SIRT4 polypeptide. In some embodiments, the cell is engineered to express a SIRT4 polypeptide that comprises amino acids 33-314 of SEQ ID NO: 2 and lacks amino acids 1-32 of SEQ ID NO: 2.

In yet a further aspect, provided are kits comprising a modulator (either an inhibitor or an activator) of SIRT4 lipoamidase activity and instructions for use of this compound for the treatment of disorders associated with dysregulation of pyruvate dehydrogenase activity. Members of other dehydrogenase complexes are also known to be modified by lipoylation, such as dihydrolipoamide branched chain transacylase (DBT) and dihydro lipoyllysine succinyltransferase (DLST). Therefore, SIRT4 modulators can also be used in the treatment of human diseases and disorders associated with the activities of branched-chain alpha-keto dehydrogenase complex and oxoglutarate dehydrogenase complex. Examples of such disorders include, but are not limited to, neurodegeneration and metabolic disorders, such as lactic acidosis and maple syrup urine disease, as well as virus infection-induced human pathologies.

In yet a further aspect, provided are kits for measuring dihydrolipoyllysine acetyltransferase (DLAT) activity in a biological sample, the kit comprising (a) a first antibody, a second antibody and optionally a third antibody, wherein the first antibody binds a first DLAT lipoamide, wherein the first antibody optionally comprises a detectable label, wherein the second antibody binds a second DLAT lipoamide, wherein the second antibody optionally comprises a detectable label, and wherein the third antibody binds SIRT4 wherein the antibody optionally comprises a detectable label; and (b) instructions for measuring DLAT activity and comparing the level of DLAT activity in the biological sample to a predetermined criterion. In some embodiments, the DLAT lipoamide is selected from the group consisting of DLAT lipoyl-K259(SEQ ID NO: 8) and DLAT lipoyl-K132 (SEQ ID NO: 7).

The term "predetermined criterion" as used herein refers to a level of lipoamidase activity or dihydrolipoyllysine acetyltransferase (DLAT) activity in a cell that does not express a SIRT4 polypeptide (i.e., a control sample). In some embodiments, the predetermined criterion includes information such as mean, standard deviation, quartile measurements, confidence intervals, or other information about the lipoamidase activity of SIRT4 (or dihydrolipoyllysine acetyltransferase (DLAT) activity) in the cell. In still other variations, the predetermined criterion is a receiver operating characteristic curve based on data of lipoamidase activity (or dihydrolipoyllysine acetyltransferase (DLAT) activity) measurements in subjects with a metabolic disorder and subjects that do not have a metabolic disorder. Optionally, the predetermined criterion is based on subjects further stratified by other characteristics that can be determined for a subject, to further refine the diagnostic precision. Such additional characteristics include, for example, sex, age, weight, smoking habits, race or ethnicity, blood pressure, other diseases, and medications.

In some embodiments, the kit further comprises instructions for measuring the relative abundance of a DLAT lipoamide in a sample using selection reaction monitoring (SRM) full-scan tandem mass spectrometry.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs herein. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus.

It should be understood that while various embodiments in the specification are presented using "comprising" language, under various circumstances, a related embodiment is also be described using "consisting of" or "consisting essentially of" language. It is to be noted that the term "a" or "an", refers to one or more, for example, "an immunoglobulin molecule," is understood to represent one or more immunoglobulin molecules. As such, the terms "a" (or "an"), "one or more," and "at least one" is used interchangeably herein.

BRIEF DESCRIPTION OF THE FIGURES

For the purpose of illustrating the invention, there are shown in the drawings embodiments which are presently preferred. It is understood, however, that the invention is not limited to the precise arrangements and instrumentalities shown in the drawings:

FIG. 4. SIRT4-EGFP localization and protein interactions. a, Confocal microscopy of SIRT4-EGFP by direct fluorescence reveals co-localization with mitochondrial stain MitoTracker. b, Bioinformatic interrogation of SIRT4 protein interactions using Reactome annotation highlights significant enrichment of pyruvate metabolism and TCA cycle components, branched chain amino acid catabolism, biotin transport and metabolism, mitochondrial fatty acid beta oxidation, and mitochondrial tRNA aminoacylation. Table contains Reactome Group Terms, the corresponding p-values for statistical enrichment versus the entire Reactome annotation, number of SIRT4 interactions (genes) assigned to each group, the percent of each annotation that these SIRT4 interactions represent relative to the total annotated genes. c, String analysis of components of pyruvate and branched-chain amino acid functional groups identifies a core cluster of proteins linked to mitochondrial dehydrogenase complexes. KEGG pathway analysis illustrates the molecular loci of SIRT4 interactions.

FIG. 7. Generation of MRC5 cells with reduced SIRT4 expression. a, Relative SIRT4 mRNA expression was measured by qRT-PCR in MRC5 cells stably expressing either non-targeting control shRNA or one of five constructs targeting SIRT4 (designated sh #1-5). Preliminary screening identified sh #5 to be the most effective in attenuating SIRT4 expression. b, SIRT4 mRNA levels were measured in triplicate by qRT-PCR and demonstrate greater than 80% knockdown compared to control cells. c, Mitochondria were purified from MRC5 cells expressing shRNA constructs (shCTL, shSIRT4#1, and shSIRT4#5) and Western blotting performed to detect SIRT4 expression.

FIG. 9 provides a list of SIRT4 interacting protein partners.

FIG. 10 provides a list of synthetic acyl-peptides.

FIG. 11 provides a list of shRNA sequences utilized in RNA interference assay provided in Example 1.

FIG. 12 provides a list of primers used in qRT-PCR assay described in Example 1.

FIG. 13. Determination of kinetic parameters for mitochondrial SIRTs. (A) Estimation of $k_{cat}/K_m$ by linear regression of $v_0/[SIRT4]$ vs. [S] for the reaction of SIRT4 with either H3K9 acetyl (left) or MCD acetyl (right). (B) Estimation of $k_{cat}/K_m$ by linear regression of $v_0/[SIRT4/5]$ vs. [S] for the reaction of SIRT4 or SIRT5 with DLAT acetyl. (C) Steady-state kinetic analysis of SIRT3 with DLAT K259 lipoyl peptide (SEQ ID NO: 8) showed lower catalytic efficiency compared to SIRT4. (D) Steady-state kinetic analysis of SIRT3 with DLAT K259 acetyl peptide (SEQ ID NO: 8) showed greater catalytic efficiency compared to SIRT4. (E) Summary comparison table of in vitro kinetics for mitochondrial SIRTs with acyl-modified DLAT K259 peptide SEQ ID NO: 8) substrates. *ND, $k_{cat}$ and $K_m$ were not calculated because $v_0$ vs. [S] was linear. $k_{cat}/K_m$ was estimated by linear regression of $v_0/[SIRT]$ vs. [S].-, unmodified product was not detected (<<0.1% of substrate as determined by mass spectrometry).

FIG. 15. Characterization of proteotyptic peptides for mass spectrometry-based parallel reaction monitoring (PRM) assay. (A) Representative MS/MS spectra of endogenous DLAT peptide containing K259 lipoyl (SEQ ID NO: 8) detected from endogenous DLAT that was immunoisolated from MRC5 mitochondria and digested with endoproteinase GluC. *Reduced and alkylated (thiol carbamidomethylation) lipoyl-lysine ($\Delta m=304$ amu vs. unmodified lysine) (B) Representative MS/MS spectra of chemically synthesized K259 lipoyl peptide (SEQ ID NO: 8) that was reduced and alkylated in vitro. (C) Representative MS/MS spectra of K132 lipoyl peptide (SEQ ID NO: 7) (reduced and alkylated, as K259 above) detected from endogenous DLAT that was immunopurified from MRC5 mitochondria and digested with endoproteinase GluC.

DETAILED DESCRIPTION

Figure 1:
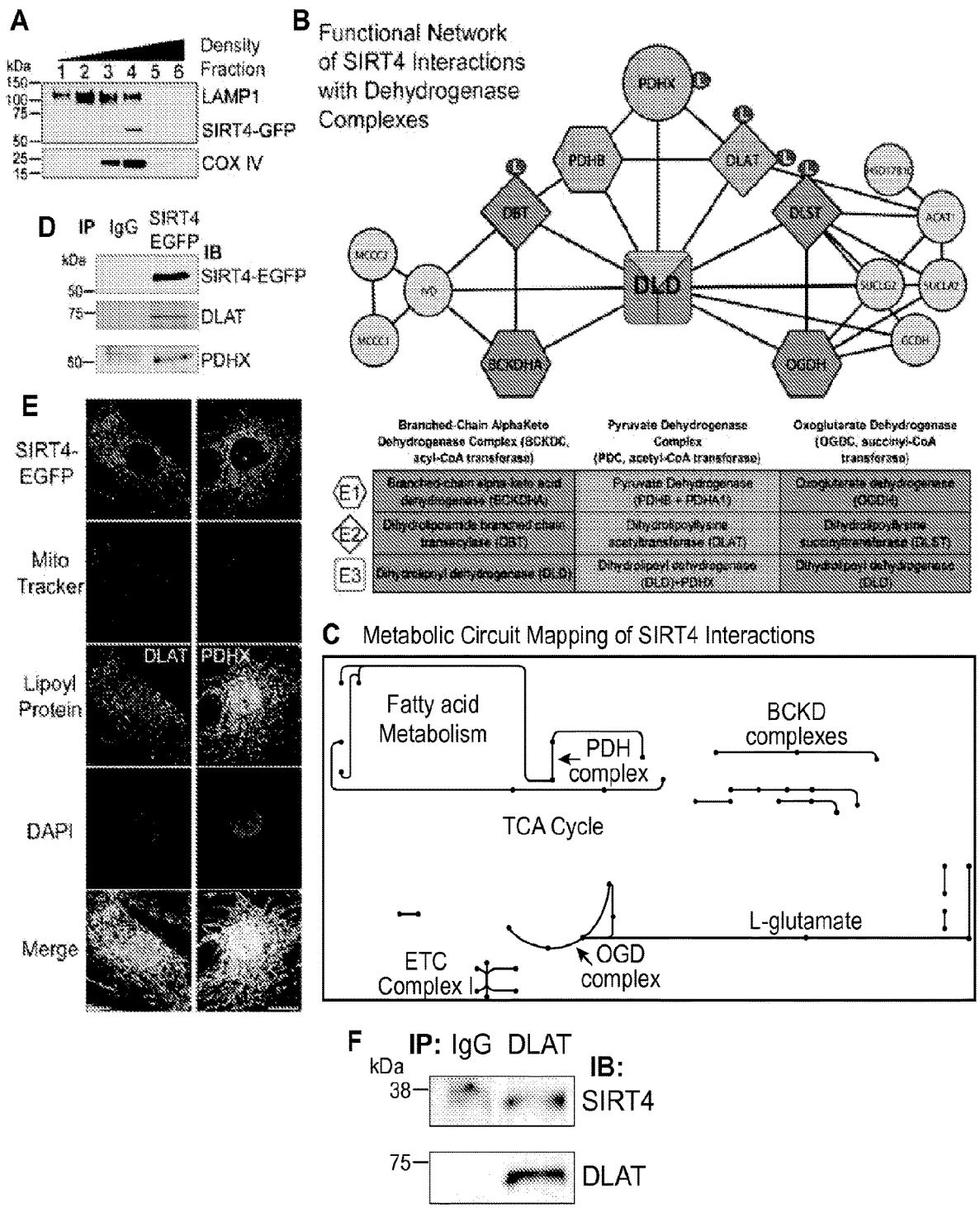
FIG. 1. SIRT4 interacts with the pyruvate dehydrogenase complex. a, Density gradient-based cellular fractionation of MRC5 cells isolates SIRT4-EGFP with mitochondrial marker COX IV. b, Functional pathway analysis of SIRT4 interactions identified by IP-MS reveals association with dehydrogenase complexes. The E2 components in each complex (diamonds) contain lipoamide modifications (circle). c, KEGG pathway analysis illustrates the molecular loci of SIRT4 interactions. d, Immunoaffinity purification of SIRT4-EGFP co-isolates DLAT and PDHX. e, SIRT4-EGFP co-localizes with DLAT and PDHX within mitochondria (MitoTracker Red). f, Reciprocal immunoaffinity purification of DLAT co-isolates endogenous SIRT4 in wild-type fibroblasts.

The present application is based on the discovery that SIRT4 acts as a cellular lipoamidase that negatively regulates pyruvate dehydrogenase complex (PDHC) activity through hydrolysis of its lipoamide cofactors. For example, data provided herein demonstrates that over-expression of SIRT4 (SIRT4-OE) in a mammalian cell diminished PDHC activity, while knock-down of SIRT4 (SIRT4-KD) elevated PDHC activity in the mammalian cell.

Since the 1960s, regulation of the PDHC, which converts pyruvate to acetyl-CoA, has been thought to be entirely based on reversible phosphorylation-dephosphorylation mechanisms[7,8]. PDHC is a complex of three enzymes that transform pyruvate into acetyl-CoA by a process called pyruvate decarboxylation. Acetyl-CoA is then used in the citric acid cycle to carry out cellular respiration. PDHC links the glycolysis metabolic pathway to the citric acid cycle.

Pyruvate decarboxylation is also known as the "pyruvate dehydrogenase reaction" because it also involves the oxidation of pyruvate.

The Examples provided herein demonstrate that SIRT4 interacts with the PDHC, and its E2 component dihydrolipoyllysine acetyltransferase (DLAT) as a biological substrate. SIRT4 modulates the cellular levels of DLAT lipoamide modifications at K132 and K259, thereby regulating overall PDHC function. As the PDHC produces acetyl-CoA to fuel downstream metabolic pathways, including the TCA cycle and fatty acid synthesis, these findings define a pathway through which SIRT4 functions as a gatekeeper of cellular metabolism. This discovery provides a foundation to better understand the involvement of SIRT4 in cancers, diabetes, and cardiovascular disease.

In one aspect, described herein is a method of modulating dihydrolipoyllysine acetyltransferase (DLAT) activity in a mammalian cell comprising contacting the cell with an agent that modulates the lipoamidase activity of a SIRT4 polypeptide, thereby modulating the DLAT activity in the mammalian cell. The term "lipoamidase activity" as used herein refers to the ability of SIRT4 to act as an enzyme which removes lipoic acid from the ε-amino group of a lysine residue in 2-oxoacid dehydrogenase complexes. The ability of SIRT4 to modify lipoyl groups of DLAT, for example, results in the negative regulation of the pyruvate dehydrogenase complex.

In some embodiments, the agent that modulates the lipoamidase activity of the SIRT4 polypeptide is selected from the group consisting of an antibody, a small molecule and an antisense oligonucleotide. In some embodiments, the agent decreases the lipoamidase activity of the SIRT4 polypeptide, thereby increasing the DLAT activity in the mammalian cell. In some embodiments, the agent increases the lipoamidase activity of the SIRT4 polypeptide, thereby decreasing the DLAT activity in the mammalian cell.

In another aspect, described herein is a method of increasing pyruvate dehydrogenase complex (PDHC) activity in a mammalian cell comprising contacting the cell with an inhibitor of SIRT4 lipoamidase activity, thereby increasing PDHC activity in the cell. In some embodiments, the cell is contacted with the inhibitor in an amount effective to increase a level of a dihydrolipoyllysine acetyltransferase (DLAT) lipoamide in the cell compared to a cell of the same type that is not contacted with the inhibitor.

In another aspect, described herein is a method of assaying lipoamidase activity of SIRT4 in a mammalian cell that expresses a SIRT4 polypeptide comprising measuring a level of a dihydrolipoyllysine acetyltransferase (DLAT) lipoamide in a cell that expresses a SIRT4 polypeptide, thereby assaying the lipoamidase activity of SIRT4 in the cell. In some embodiments, the cell comprises a decreased level of a DLAT lipoamide compared to a cell of the same type that does not express a SIRT4 polypeptide.

In another aspect, described herein is a method of assaying lipoamidase activity of SIRT4 in a tissue sample, wherein the tissue sample comprises a cell that expresses a SIRT4 polypeptide, the method comprising measuring a level of a dihydrolipoyllysine acetyltransferase (DLAT) lipoamide in the tissue sample, thereby assaying the lipoamidase activity of SIRT4 in the cell. In some embodiments, the tissue sample comprises a decreased level of a DLAT lipoamide compared to a tissue of the same type that does not express a SIRT4 polypeptide.

In any of the methods described herein, in some embodiments, the DLAT lipoamide is selected from the group consisting of DLAT lipoyl-K259 (SEQ ID NO: 8) and DLAT lipoyl-K132 (SEQ ID NO: 7).

In some embodiments, measuring the lipoamidase activity of the SIRT4 polypeptide comprises measuring a level of DLAT lipoamide in a cell (or tissue sample) that expresses a SIRT4 polypeptide using a method as described in Example 2. For example, in some embodiments, the method comprises measuring a level of DLAT lipoyl-K259 (SEQ ID NO: 8) and/or DLAT lipoyl-K132 (SEQ ID NO: 7) in the cell (or tissue sample). An increased level of a DLAT lipoamide in the cell (or tissue sample) is indicative of a decreased level of SIRT4 lipoamidase activity in the cell (or tissue sample). Other methods of assessing the lipoamidase activity of an enzyme are known in the art. See, for example, Wang et al., Inflamm. & Regen., 31:88-94, 2011, the disclosure of which is incorporated herein by reference in its entirety.

As used herein, the term "SIRT4 polypeptide" relate to wild type SIRT4, to a mutant SIRT4, a variant SIRT4, and to biologically-active fragments and mature forms thereof. In some embodiments, the SIRT4 polypeptide is a human SIRT4 polypeptide. The amino acid sequence of human SIRT4 comprises 314 amino acids and is set forth in SEQ ID NO: 2 and also as GenBank Acc. No. NP_036372. The polynucleotide sequence encoding human SIRT4 polypeptide is set forth in SEQ ID NO: 1.

Fragments of SIRT4 polypeptides are also contemplated for use in the methods described herein. The term "fragment of SIRT4" refers to a polypeptide that includes a sufficient portion of the wild type SIRT4 such that the polypeptide retains the lipoamidase activity and its impact on the PDHC that is demonstrated in Examples 1 and 2. The fragment optionally is attached to heterologous sequences that do not eliminate this enzymatic activity. In some embodiments, the SIRT4 fragment comprises amino acids 33-314 of SEQ ID NO: 2 and lacks amino acids 1-32 of SEQ ID NO: 2.

In any of the methods described herein, in some embodiments, the mammalian cell (or tissue sample) expresses an endogenous SIRT4 polypeptide. In other embodiments, the cell has been engineered to express a SIRT4 polypeptide or fragment thereof (e.g., a fragment comprising amino acids 33-314 of SEQ ID NO: 2 and lacking amino acids 1-32 of SEQ ID NO: 2).

Also provided herein is the use of a SIRT4 polypeptide (or active fragment thereof) in the screening of compounds that modulate the lipoamidase activity of a SIRT4 polypeptide (or active fragment thereof), which in turn modulates the expression of components of the pyruvate dehydrogenase complex (PDHC), such as dihydrolipoyllysine acetyltransferase (DLAT). Such modulators and particularly inhibitors of SIRT4 lipoamidase activity are useful as therapeutic agents for the treatment of, for example, metabolic disorders.

For example, described herein is a method for identifying a candidate agent that increases dihydrolipoyllysine acetyltransferase (DLAT) activity in a mammalian cell that expresses a SIRT4 polypeptide, the method comprising contacting the cell with the candidate agent; and measuring SIRT4 lipoamidase activity in the cell, wherein a decreased level of SIRT4 lipoamidase activity in the cell relative to a predetermined criterion identifies the agent as an agent that increases DLAT activity in the cell. In some embodiments, measuring the lipoamidase activity of the SIRT4 polypeptide comprises measuring a level of a DLAT lipoamide in a cell that expresses a SIRT4 polypeptide using a method as described in Example 2. For example, in some embodiments, the method comprises measuring a level of DLAT lipoyl-K259 (SEQ ID NO: 8) and/or DLAT lipoyl-K132 (SEQ ID NO: 7) in the cell. An increased level of a DLAT lipoamide in the cell is indicative of a decreased level of SIRT4 lipoamidase activity in the cell. Other methods of assessing the lipoamidase activity of an enzyme are known in the art. See, for example, Wang et al., Inflamm. & Regen., 31:88-94, 2011, the disclosure of which is incorporated herein by reference in its entirety.

In some embodiments, the candidate agent is selected from the group consisting of an antibody, a small molecule and an antisense oligonucleotide.

To identify a candidate agent as being capable of inhibiting SIRT4-dependent lipoamidase activity, the lipoamidase activity present in the cell that expresses a SIRT4 polypeptide in the absence of the candidate agent is determined. One would then add the candidate agent to the cell and determine the lipoamidase activity of the SIRT4 polypeptide in the presence of the candidate agent. After comparing the levels of lipoamidase activity observed in the presence and absence of the candidate agent, an agent capable of inhibiting SIRT4-dependent lipoamidase activity can be identified. Exemplary assays are described in Example 2.

Methods of identifying modulators of the PDHC in both in vitro and in vivo formats in both the presence and absence of the candidate agents are also contemplated. It is contemplated that this screening technique will prove useful in the general identification of compounds of therapeutic value against e.g., metabolic disorders. In some embodiments, it will be desirable to identify inhibitors of SIRT4 lipoamidase activity. In other embodiments, stimulators of such activity also may be desirable.

Candidate Agents

As used herein the term "candidate agent" refers to any molecule that is capable of modulating the lipoamidase activity of a SIRT4 polypeptide. The candidate agent may be a protein or fragment thereof, a small molecule inhibitor, or even a nucleic acid molecule. The candidate agent may include a fragment or part of naturally-occurring compound or may be only found as active combinations of known compounds which are otherwise inactive. However, prior to testing of such compounds in humans or animal models, it will be necessary to test a variety of candidates to determine which have potential.

It will be understood that the candidate agents to be screened could also be derived or synthesized from chemical compositions or man-made compounds. Thus, it is understood that the candidate agent identified by a method described herein may be polypeptide, polynucleotide, small molecule inhibitors or any other inorganic or organic chemical compounds that may be designed through rational drug design starting from known agents that are used in the intervention of a metabolic disorder.

The candidate agent screening assays are simple to set up and perform. Thus, in assaying for a candidate substance, the method comprises contacting a cell that expresses a SIRT4 polypeptide with a candidate agent in an amount effective to and under conditions which would allow measurable lipoamidase activity to occur. An exemplary assay for measuring the lipoamidase activity of the SIRT4 polypeptide is set forth in Example 2. In this fashion the ability of the candidate agent to reduce, abolish, or otherwise diminish a biological effect mediated by the SIRT4 polypeptide from said cell may be detected.

"Effective amounts" in certain circumstances are those amounts effective to reproducibly alter SIRT4-dependent lipoamidase-associated activity of the cell in comparison to the normal levels of such an event. Compounds that achieve significant appropriate changes in such activity will be used.

The identification of a candidate agent that is capable of causing at least about 30%-40% reduction in SIRT4-mediated lipoamidase activity in a cell is specifically contemplated. Candidate agents that cause at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95% or more reduction in SIRT4-mediated lipoamidase activity are also contemplated.

Potential protein candidate agents are often used in high throughput screening (HTS) assays, such as the HTS assay described in Example 1. Other HTS assays are known in the art, and include melanophore assays to investigate receptor ligand interactions, yeast based assay systems and mammalian cell expression systems. For a review see Jayawickreme and Kost, Curr. Opin. Biotechnol. 8: 629 634 (1997). Automated and miniaturized HTS assays are also contemplated as described for example in Houston and Banks Curr. Opin. Biotechnol. 8: 734 740 (1997).

There are a number of different libraries used for the identification of small molecule modulators including chemical libraries, natural product libraries and combinatorial libraries comprised or random or designed peptides, oligonucleotides or organic molecules. Chemical libraries consist of structural analogs of known compounds or compounds that are identified as hits or leads via natural product screening or from screening against a potential therapeutic target. Natural product libraries are collections of products from microorganisms, animals, plants, insects or marine organisms which are used to create mixtures of screening by, e.g., fermentation and extractions of broths from soil, plant or marine organisms. Natural product libraries include polypeptides, non-ribosomal peptides and non-naturally occurring variants thereof. For a review see Science 282:63 68 (1998). Combinatorial libraries are composed of large numbers of peptides oligonucleotides or organic compounds as a mixture. They are relatively simple to prepare by traditional automated synthesis methods, PCR cloning or other synthetic methods. Of particular interest will be libraries that include peptide, protein, peptidomimetic, multiparallel synthetic collection, recombinatorial and polypeptide libraries. A review of combinatorial libraries and libraries created therefrom, see Myers Curr. Opin. Biotechnol. 8: 701 707 (1997). A candidate modulator identified by the use of various libraries described may then be optimized to modulate lipoamidase activity of a SIRT4 polypeptide through, for example, rational drug design.

Those of skill in the art are aware of in vitro methods for measuring lipoamidase activity. See, for example, Wang et al., Inflamm. & Regen., 31:88-94, 2011. Cells that endogenously express a SIRT4 polypeptide, e.g., a MRC-5 cell, or cell (from any eukaroyotic, preferably mammalian source) that has been transformed or transfected with a nucleic acid that encodes a protein of SEQ ID NO:2 are obtained as described in Example 1. The cells are cultured in DMEM containing 10% (v/v) Benchmark fetal bovine serum and 1% (v/v) penicillin-streptomycin solution, and maintained at 37° C. with 5% $CO_2$. To measure lipoamidase activity, mictochondria are isolated from the MRC-5 cells and lysed. The mitochondrial lysates are pooled and subjected to nLC-SRM-MS/MS assays as described below in Example 2.

The IC50 values of the tested candidate agents may be determined using an assay such as the one set forth above or any other conventional assay that measures lipoamidase activity. Compounds that are effective in such in vitro assays may be tested in subsequent in vivo assays as described below.

Other forms of in vitro assays include those in which functional readouts are taken. For example cells in which a SIRT4 polypeptide is expressed can be treated with a candidate agent. In such assays, the substance would be formulated appropriately, given its biochemical nature, and contacted with the cell. Depending on the assay, culture may be required. The cell may then be examined by virtue of a number of different physiologic assays. Alternatively, molecular analysis may be performed in which the cells characteristics are examined. This may involve assays such as those for protein expression, enzyme function, substrate utilization, mRNA expression (including differential display of whole cell or polyA RNA) and others. Yet another assay format that can be contemplated is the use of a binding assay with a suitably labeled ligand that binds to the expressed SIRT4 polypeptide. An example of such an assay would be the displacement by a small molecule of a radiolabeled or fluorescently labeled ligand from the expressed SIRT4 polypeptide. Such an assay can be used to identify potential small molecule modulators especially if the site where the labeled ligand binds is known to affect lipoamidase activity or regulation.

The invention may be more readily understood by reference to the following examples, which are given to illustrate the invention and not in any way to limit its scope.

EXAMPLES

Example 1—Materials and Methods

Generation of MRC5-Derivative Stable Cell Lines.

MRC5 cells and stable cell line derivatives were cultured in DMEM (Life Technologies, cat. #11965-084) containing 10% (v/v) Benchmark fetal bovine serum (Gemini Bio-products, cat. #100-101) and 1% (v/v) penicillin-streptomycin solution (Gibco, cat. #15070-063), and maintained at 37° C. with 5% CO2.

EGFP and SIRT4-EGFP Expression.

pLXSN vector containing SIRT4-EGFP ORF was cloned from pcDNA3.1(+) SIRT4 plasmid (Addgene, plasmid #13815). The SIRT4 gene was PCR-amplified using primers specified in Supplementary Table 4, and digested with XhoI and BamHI. Digested product was ligated into the 5' end of EGFP ORF (pEGFP-N1, cloned into LXSN plasmid (Clontech, cat. #631509). pLXSN SIRT4-EGFP H161Y mutant was generated using QuickChange Mutagenesis Kit (Agilent, cat. #210518) with primers listed in Supplementary Table 4. To generate MRC5 cells stably expressing SIRT4-EGFP, Phoenix cells were transfected with pLXSN SIRT4-EGFP plasmid using FuGENE 6 (Roche, cat. #11815091001). Upon production of the retroviral particles, the media was used to transduce MRC5 cells, which were subsequently selected with 400 μg/mL G418 (EMD Millipore, cat. #345810) and sorted by fluorescence-activated cell sorting using Vantage S.E. with TurboSortII (Becton Dickinson). SIRT4 expression levels were measured by qRT-PCR.

Sirt4 shRNA Expression.

pLKO.1-puro vectors containing either non-targeting control shRNA or SIRT4-targeting shRNA were purchased from Sigma-Aldrich and are listed in FIG. 11. To generate MRC5 cells stably expressing each of the shRNA constructs, HEK293T cells were co-transfected with appropriate pLKO.1 vector, pCMVΔR8.2 (Addgene, plasmid #12263) and pMD2.G (Addgene, plasmid #12259) using FuGENE 6. Media containing lentivirus particles were used to transduce MRC5 cells, which were subsequently selected with 2 μg/mL puromycin (InvivoGen, cat. # ant-pr-1). Knockdown efficiency was measured by qRT-PCR and western blotting.

Transient Transfection of HEK 293 Cells.

HEK293 cells were transfected with either of the following vectors: pCDNA3 mCherry (Addgene), pCDNA3.1(+) SIRT4-FLAG (Addgene), pCDNA3.1(+) SIRT4-FLAG H161Y (generated by site-directed mutagenesis from pCDNA3.1(+) SIRT4-FLAG). Transfections were performed using Lipofectamine 2000 (Invitrogen, cat. #11668-019) reagent according to the manufacturer's protocol. Cells were collected at 48 hours post transfection and processed for downstream experiments.

qRT-PCR Analysis.

For qRT-PCR analysis, MRC5 cells were collected and washed with PBS. Total RNA was isolated from cell pellets using RNeasy Mini Kit (Qiagen, cat. #74104) and the concentration/purity determined by measuring the absorbance 260/280 nm using NanoDrop Spectrophotometer (Thermo Fisher Scientific). For cDNA synthesis, 1 μg of RNA from each sample was first treated with DNase I (Life Technologies, cat. #18068015) and then used as a template in the RETROscript kit (Life Technologies, cat. # AM1710). The cDNAs were mixed with appropriate primers listed in FIG. 12 and Power SYBR green PCR master mix (Life Technologies, cat. #4368706) for qRT-PCR on ABI 7900HT Real-Time Thermocycler (Applied Biosystems). Data analysis was performed using RQ Manager 1.2 (Applied Biosystems).

Confocal Microscopy.

For live imaging, MRC5 cells stably expressing SIRT4-EGFP were grown on glass-bottom dishes coated with Poly-D-Lysine (MatTek Corporation, cat. # P35GC-1.5-14-C) and treated with MitoTracker Red CMXRos (Life Technologies, cat. # M-7512) according to manufacturer's instructions. Imaging was performed on a Leica SP5 confocal microscope using the 63× oil immersion objective.

For co-localization studies, MRC5 stably expressing SIRT4-EGFP cells were first treated with MitoTracker Red CMXRos, washed with PBS, fixed with 4% (v/v) formaldehyde at RT for 15 min, and permeabilized with ice-cold methanol for 15 min. After washing with 0.2% (v/v) Tween-20 in PBS (PBST), cells were blocked with 2% (w/v) BSA in PBST for 1 hr at RT. After blocking, samples were probed with either rabbit anti-DLAT or rabbit anti-PDHX (Santa Cruz Biotechnology, cat. # sc-32925 and sc-98752) antibodies diluted in 2% BSA/PBST overnight at 4° C. After washing with PBST, samples were incubated with goat anti-rabbit antibodies conjugated to Alexa Fluor 647 (Life Technologies, cat. # A20991). Finally, the cells were washed with PBST and incubated with 1 μg/mL DAPI in PBST for 30 min. Samples were then washed and kept in PBST until imaging was performed on the Leica SP5 confocal microscopy using the 63× glycerol immersion objective.

Mitochondrial Isolation.

MRC5 cells ($25 \times 10^6$) were cultured to 90% confluence, trypsinized, washed with PBS, and resuspended in 4 mL Homogenization Medium (0.25 M sucrose, 1 mM EDTA, 20 mM Hepes-NaOH, pH 7.4). Cells were then lysed by pressure filtration using 14 μM Hydrophilic Polycarbonate Membrane Filters (Steriltech, cat. # PCT14013100). Nuclei were removed by centrifugation at 1,400×g for 10 min at 4°

C., and a crude organelle pellet collected by centrifugation at 20,000×g for 30 min at 4° C. Crude organelles were resuspended in 0.7 mL Homogenization Medium and layered on-top of a 3.6 mL 10-30% discontinuous Iodixanol OptiPrep™ gradient (Sigma Aldrich, cat. # D1556) in 0.25 M sucrose, 6 mM EDTA, 120 mM Hepes-NaOH, pH 7.4. Ultracentrifugation was performed at 100,000×g for 3 hr at 4° C. using a SW60 rotor (Beckman Coulter), and 6×0.7 mL gradient fractions were collected sequentially starting from the top of the gradient. Each fraction was washed twice with PBS, and re-pelleted by centrifugation at 20,000×g for 30 mins at 4° C. The density of each fraction was determined from a duplicate parallel discontinuous OptiPrep™ gradient overlaid with 0.7 mL Homogenization Medium. Similarly, each fraction was collected, diluted 10,000-fold with water, and the absorbance measured at 244 nm. Mitochondria were isolated in fractions 3-4 based on Western immunoblotting. These fractions were pooled and used for immunopurifications and nLC-SRM-MS/MS assays, as described below. Protein concentration of each fraction was determined using the Bradford assay.

Western Immunoblotting.

10 μg of protein from each fraction was resuspended in 20 μL SDS Sample Buffer. Each sample was subjected to SDS-PAGE, transferred to nitrocellulose membranes (GE Healthcare Life Sciences, cat. #45-000-929), and blocked in blocked in 5% (w/v) skim milk powder in Tris-buffered saline with 0.05% (v/v) Tween-20 (TBST) for 1 hr at RT. Membranes were probed according to manufacturer's instructions, with the following primary antibodies: mouse anti-GFP (Roche, cat. #11814460001), rabbit anti-LAMP1 (Abcam, cat. # ab24170), rabbit anti-COXIV (Cell Signaling Technology, cat. #4844), rabbit anti-DLAT (Santa Cruz Biotechnology, cat. # sc-32925), or rabbit anti-PDHX (Santa Cruz Biotechnology, sc-98752), for 1 h in TBST, followed by 1 hr incubation in corresponding horseradish peroxidase (HRP)-conjugated secondary antibodies (Jackson ImmunoResearch Laboratories). All antibody incubations were carried out at RT with gentle agitation, and blots washed three times with TBST for 10 min after each incubation. Immuno-targets were detected using ECL (GE Healthcare Life Sciences, cat. # RPN2106).

Detection of endogenous SIRT4 was achieved by immuno-blotting against 30 μg of purified mitochondria using rabbit anti-SIRT4 (Santa Cruz Biotechnology, cat. # sc-135053). Levels of lipoylated DLAT were measured using rabbit anti-lipoic acid antibody (Millipore, cat. #437695).

Immunoaffinity Purification.

SIRT4-EGFP and control EGFP immunoaffinity purifications (IPs) from MRC5 cells were performed using M270 Epoxy Dynabeads (Invitrogen, cat. #14302D) coupled with in-house generated rabbit anti-GFP polyclonal antibodies, as described previously[29]. Pooled mitochondria from fractions 3 and 4 from the OptiPrep™ gradient were resuspended in 1 mL optimized Lysis Buffer (20 mM HEPES-KOH, pH 7.4, 0.1 M KOAc, 2 mM $MgCl_2$, 0.1% Tween-20, 1 μM $ZnCl_2$, 1 μM CaCl2), with 0.6% Triton X-100, 200 mM NaCl, and 1/100 (v/v) protease inhibitor cocktail (Sigma, cat. # P8340). Lysed mitochondria were vortexed three times for 20 sec each, and mixed by rotation for 10 min at 4° C. Insoluble material (pellet) was removed by centrifugation at 5000×g for 10 min. The supernatant was collected and SIRT4-EGFP or free EGFP (negative control) was immunoisolated by incubation with 7 mg of GFP-coupled magnetic beads for 60 min at 4° C. The magnetic beads containing protein complexes were then washed four times with Lysis Buffer and twice with DPBS. Washed beads were then incubated with 30 μL of SDS Sample Buffer for 10 min at 70° C., followed by shaking for 10 min at room temperature. Immunoisolates were recovered and stored at −20° C. until further processing. Each IP was performed with two biological replicates for SIRT4-EGFP or EGFP.

Isolation of endogenous PDH was performed using PDH Immunocapture Kit (Abcam, cat. # ab109802), according to manufacturer's instructions.

Proteomic Analysis and Identification of Binding Partners.

SIRT4 immunoisolates were reduced with 50 mM dithiothreitol, alkylated with 100 mM iodoacetamide, and resolved by 4-12% BisTris SDS-PAGE. A total of six individual gel bands (~3 mm each) were excised and subjected to in-gel digestion with 125 ng trypsin in 50 mm ABC for 6 h at 37° C. Peptides were extracted using 0.5% formic acid, concentrated by vacuum centrifugation, and desalted on Stage Tips using Empore $C_{18}$ extraction discs (3M Analytical Biotechnologies, cat. #2215). Eluted peptides were analyzed by nLC-MS/MS using a Dionex Ultimate 3000 RSLC coupled directly to an LTQ-Orbitrap Velos ETD mass spectrometer (ThermoFisher Scientific). Peptides were separated by reverse phase chromatography using Acclaim PepMap RSLC, 1.8 μm, 75 μm×25 cm (Dionex, cat. #164536) at a flow rate of 250 nl/min using a 90-min discontinuous gradient of ACN as follows: 4% to 16% B over 60 min, 16% to 40% B over 30 min (Mobile phase A: 0.1% formic acid in water, Mobile phase B: 0.1% formic acid in 97% ACN).

The mass spectrometer was operated in data-dependent acquisition mode with FT preview scan disabled and predictive AGC and dynamic exclusion enabled (repeat count: 1, exclusion duration: 70 s). A single acquisition cycle comprised a single full-scan mass spectrum (m/z=350-1700) in the orbitrap (resolution=30,000 at m/z=400), followed by collision-induced dissociation (CID) fragmentation of the top 20 most intense precursor ions (min signal=1E3) in the dual-pressure linear ion trap. FT full scan MS and IT MS2 target values were 1E6 and 5E3, and maximum injection times were set at 300 and 100 ms, respectively. CID fragmentation was performed at an isolation width of 2.0 Th, normalized collision energy of 30, and activation time of 10 ms.

MS/MS spectra were extracted, filtered, and searched by Proteome Discoverer/SEQUEST (v1.3 ThermoFisher Scientific) against a human protein sequence database (UniProt-SwissProt, 2010-11) appended with common contaminants (21,570 entries), which were automatically reversed and concatenated to the forward sequences. Spectra were searched with the following criteria: full enzyme specificity; 2 missed cleavages; precursor mass tolerance: 10 ppm; fragment mass tolerance: 0.5 Da; static modification of carbamidomethylcysteine (+57 Da), variable modifications of methionine oxidation (+16 Da), phosphoserine, threonine, and tyrosine (+80 Da), and acetyl-lysine (+42 Da). For comparative proteomic analyses, SEQUEST search results were analyzed by Scaffold (v3.3.1; Proteome Software) and a refinement search using X!Tandem (Beavis Informatics). Probabilities for peptide spectral matches were calculated using PeptideProphet in Scaffold. Probability filters were selected empirically to reduce the global peptide and protein false discovery rate to less than 1%.

Significance Analysis of INTeractome (SAINT).

Interaction scoring using SAINT v. 2.3 contained the following information for each prey protein: prey gene symbol, protein accession number, protein length, and the spectral counts (total counts) for each purification (or control run). The SAINT parameters were used: lowmode=0, minford=1, and norm=1. The spectral count of the bait protein in its own purification was set to zero. SAINT was run separately for each IP, and SAINT results were merged into a single data table using an in-house written script. For each experiment, SAINT computed the individual probability for each biological replicate (iProb). The final SAINT score for each bait-prey pair was taken as an average of the individual SAINT probabilities. Prey proteins with a SAINT score of greater than or equal to 0.95 were considered putative protein interactions.

Recombinant SIRT4 Protein Expression and Purification.

N-terminally truncated human Sirt4 (33-314 of SEQ ID NO: 2) was cloned into a derivative of pET-15b containing a human rhinovirus 3C Protease cleavage site in place of its thrombin cleavage site. 6×His-Sirt4 was co-expressed with GroEL and GroES in BL21(DE3) $E.$ $coli$ in order to promote proper protein folding. Protein was purified using immobilized-metal affinity chromatography (IMAC) followed by anion-exchange chromatography to remove associated folding chaperones. For some experiments the His-tag was removed using 3C protease. Protein was concentrated, snap frozen in $N_{2(l)}$, and stored at $-80°$ C.

Recombinant SIRT3 (Sigma, cat. # SRP0117-100UG) and SIRT5 (Sigma, cat. # SRP0119-100UG) were purchased from Sigma.

Peptide Synthesis.

Synthetic peptides were designed (FIG. 10) the synthesis performed by GenScript. Peptides were resuspended according to GenScript's recommendations, and the concentration determined by absorbance at 280 nm using the tryptophan extinct coefficient (5560 $M^{-1}cm^{-1}$). For structural validation, peptides were infused into an LTQ Orbitrap XL or Velos mass spectrometer equipped with a nanospray Flex ionization source (ThermoFisher Scientific).

LC-MS-Based In Vitro Peptide Deacylation Assay.

The ability of SIRT4 to hydrolyze various acyl-lysine modifications was measured using LC-MS. In 20 µL reaction volume, 10 uM peptide (lipoyl-, biotinyl-, or acetyl-lysine) was incubated with increasing concentrations of SIRT4 (0.5 µM, 2.5 µM, and 5 µM), with or without NAD, in 50 mM TrisHCl, pH 8, 137 mM NaCl, 2.7 mM KCl and 1 mM MgCl2, for 1 hr at 37° C. Reactions were quenched with 25 µL of 2% TFA and an internal control peptide was spiked in to monitor for run-to-run variability. Reaction products were desalted, eluted, concentrated and analyzed by nano-LC-MS/MS, as above, but altered LC gradients. A 30 min linear gradient from 4-40% B was used for all peptides, except for lipoyl-lysine biological peptides, which used a 12-70% B linear gradient. Data were imported into Skyline software (version 2.1) to obtain precursor extracted ion chromatographams (XICs) using the following settings: Isotope Count, 3; precursor mass analyzer, Orbitrap; Resolving power, 60,000 @ 400 Th. The retention times of substrate (modified) and product (unmodified) peptides were confirmed by fragmentation spectra and peak integration boundaries were manually inspected. Three biological replicates were analyzed for each reaction.

HPLC-Based SIRT4 Kinetics Assays.

SIRT4 kinetic assays were essentially performed as described by others[3,4]. Briefly, enzyme reactions (20 µL) were performed in 50 mM Tris, pH 8.0, containing 5 µM recombinant SIRT4 and varying concentrations (0 to 2500 µM) of H3K9- or DLAT-modified peptides with either acetyl-lysine, biotinyl-lysine, or lipoyl-lysine. Reactions were initiated by addition of NAD (1 mM) and incubated at 25° C. for between 30-120 min, depending on substrate-specific reaction rates and to maintain steady-state conditions. Reactions were quenched with formic acid to a final concentration of 0.5% (v/v) and analyzed by HPLC-UV detection (Ultimate 3000 RSLC/VWD-3400). Substrate and product were separated by reverse-phase chromatography (Acclaim PepMap RSLC, 75 µm×15 cm) at 0.75 µL/min. Product concentration was measured by peak integration of $A_{280}$ signals. Initial reaction velocities were determined in at least duplicate and fit to a modified Briggs-Haldane equation, which substituted $k_{cat} \times [SIRT4]$ for $V_{max}$ and allowed determination of kinetic parameters, $k_{cat}$, $K_m$ and $k_{cat}/K_m$ and their associated error (±SEM), using GraphPad Prism 5.

Lipoyl-Lysine SRM Assay.

The relative abundance of lipoyl-lysine-containing peptides identified from immunoisolated, in-gel digested DLAT (described above) was measured in mitochondria lysates using a selected reaction monitoring (SRM) full-scan tandem mass spectrometry assay. Purified mitochondria were isolated from MRC5 stable cell lines expressing EGFP, SIRT4-EGFP, and SIRT4-targeting shRNA (described above). Mitochondria pellets were lysed by agitation and bath sonication in 100 µL of hot (95° C.) buffer containing 0.1 M ammonium bicarbonate, 5 mM tris(2-carboxyethyl) phosphine, 1 mM nicotinamide, and 0.1% RapiGest. Protein concentration was determined using the Bradford reagent (Sigma). Lysates were heated at 70° C. for 10 min, alkylated at RT with 10 mM chloroacetamide or n-ethylmaleimde at 37° C. for 45 min, and quenched with 10 mM cysteine for 15 min at RT. Aliquots of protein (40 µg in 40 µL) were digested with 800 ng of endoproteinase GluC (Thermofisher Scientific) for 3 hours at 37° C., followed by an additional 800 ng of GluC overnight at 37° C. Digests were quenched and RapiGest hydrolyzed by addition of 4 uL of 10% formic acid and incubation for 30 min at 37° C. Quenched digests were split into 3 equal aliquots and fractionated over $C_{18}$-strong cation exchange (SCX) Stage Tips as described[30], but with modification to the elution buffers. Desalted peptides were eluted from the $C_{18}$ phase and bound to the SCX phase in 0.5% formic acid containing 80% acetonitrile (flow-through). Lipoyl-lysine-containing peptides were eluted in 25 mM ammonium formate containing 20% acetonitrile. A second elution with 25 mM ammonium acetate in 20% acetonitrile was collected. Eluates from the same sample were pooled and concentrated to near-dryness, diluted to 8 µL, and half were analyzed by an LC-SRM-MS/MS assay on an LTQ Orbitrap Velos mass spectrometry (Thermofisher Scientific). Peptides were resolved by nLC, as described above, except a 3 hr linear gradient from 4 to 35% B was employed. The mass spectrometer was configured to sequentially isolate precursor ions (2.5 Da window) and acquire full scan MS/MS spectra by collision-induced dissociation (normalized collision energy=30%) in the ion trap (target value 1E4 @ 150 ms max). Each set of MS/MS acquisitions was followed by a precursor scan in the orbitrap (resolution=7500). Data were imported into Skyline to extract precursor-product ion chromatograms (XICs) and calculate peak areas using the 'targeted' acquisition method and QIT analyzer setting @ 0.6 Da resolution. At least four co-eluting XICs (dot-product score of >0.95) were used for peak area quantification. Peak picking and integration boundaries were manually inspected. Peak areas were summed across XICs, exported to Excel, and normalized across biological replicates (n=3-6) using the average chromatographic precursor intensity calculated by RawMeat (Vast Scientific, Inc). Statistical significance was determined by unpaired, two-tailed t-tests in Microsoft Excel.

PDH Activity Assay.

The activity of the PDHC in MRC5 derivate cell lines was measured using the Pyruvate Dehydrogenase Enzyme Activity Microplate Assay Kit (Abcam, cat. # ab109902) according to manufacturer's instructions. 1000 µg/well of cultured cell extract from each line being tested was used as input for PDHC binding, and 5 µg/well of pyruvate dehydrogenase from porcine heart (Sigma-Aldrich, cat. # P7032) used as a positive control for the assay. PDH activity was measured by reduction of NAD+ to NADH, coupled to the reduction of a reporter dye to yield a colored reaction product with an increase in absorbance at 450 nm at room temperature. Assays were performed using at least three biological replicates of each cell line. Statistical significance was assessed by one-way ANOVA in GraphPad Prism 5.

For PDH activity measurements from stable MRC5 cell lines, mouse liver mitochondria, and purified porcine heart PDH (Sigma-Aldrich, cat. # P7032), 1000, 100, and 5 µg of protein extract per well, respectively, was used as input for PDH immunocapture.

Purified porcine heart PDH pre-incubated at a final concentration of 1 µg/µl (10 and 25 µL reactions for PDH assay and Western blot, respectively) in 1×PDH assay buffer for 10 min at 30° C. containing 2 mM $CaCl_2$), with or without 0.1 µg/µL of pyruvate dehydrogenase phosphatase catalytic subunit 1 (PDP1, Abcam, cat. # ab110357). To reactions that were treated with PDP1, either NAD alone (5 mM), recombinant SIRT4 (50 µM)+NAD (5 mM), or recombinant SIRT4 H161Y (50 µM)+NAD (5 mM) were added and incubated for an additional 1 hr at RT. 10 µL reactions were diluted with 400 µL of 1×PDH assay buffer and 2×200 µL were used to determine PDH activity. For Western blot analysis (25 µl reactions), 5 µg of purified porcine PDH was mixed in 1× reducing LDS sample buffer, heated at 70° C. for 10 min, resolved by SDS-PAGE, and then proteins were transferred to nitrocellulose membranes for detection of total E1α, pS232, pS293, and pS300 (see western immunoblotting above).

Animal Studies.

Animal experiments in mice were conducted in compliance with Institutional Animal Care and Use Committee (IACUC) of Princeton University. For all experiments, SIRT4 knock-out (Jackson Laboratory, Stock number 012756), and control (WT) (Jackson Laboratory, Stock number 002448) mice were utilized. Adult female mice were euthanized and organs were collected following standard procedures. Isolation of mouse liver mitochondria was performed from fresh liver tissue as previously described (35) with minor modifications. Briefly, livers were minced, washed, and homogenized in ice-cold MSHE/BSA buffer containing 210 mM mannitol, 70 mM sucrose, 5 mM HEPES-KOH, pH 7.4, 2 mM EGTA, 0.5% fatty acid-free BSA, and EDTA-free Complete protease inhibitor cocktail (Roche). Minced liver tissue was homogenized by 8-10 strokes in a Tenbroeck tissue grinder. Homogenates were centrifuged for 10 min at 600 g. The resulting pellets were homogenized and centrifuged as above. The supernatants were pooled and centrifuged at 15,000 g for 10 min. Pellets containing crude mitochondria were washed once with MSHE/BSA, and twice with BSA-free MSHE buffer. Aliquots of mitochondrial pellets were resuspended in PBS to determine protein content prior to PDH activity measurements.

Example 2—SIRT4 Demonstrated Lipoamidase Activity

Figure 8:
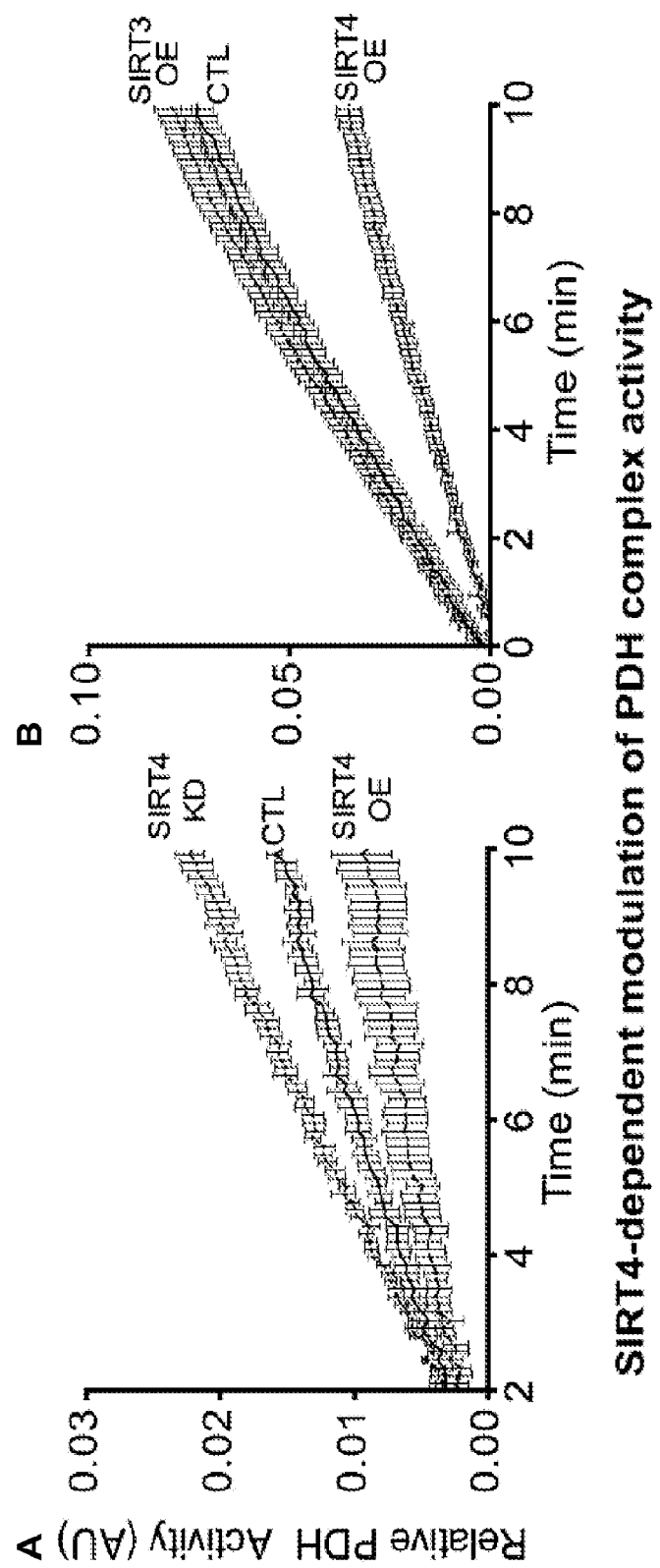
FIG. 8. SIRT4-dependent modulation of PDH complex activity. a, Relativity activity was measured following immuno-capture of intact PDHC in a microwell plate. The ability of bound PDHC to reduce NAD+ to NADH was coupled to production of reporter dye that was detected by absorbance at 450 nm over time. Slope of linear regression curves was used to calculate relative PDHC activity (versus control, CTL). Over-expression of SIRT4 (SIRT4-OE) diminished PDH activity, while knock-down of SIRT4 (SIRT4-KD) elevated activity. b, Over-expression of SIRT4 but not SIRT3.

To investigate potential endogenous substrates of SIRT4, proteomics was used to define its endogenous mitochondrial protein interactions. Given recent SIRT4 studies in mouse embryonic fibroblasts[16], MRC5 fibroblasts stably expressing SIRT4-EGFP were constructed as described above in Example 1. Using direct fluorescence microscopy (co-localization with MitoTracker, FIG. 4) and density-based organelle fractionation (co-isolation with the mitochondrial COX IV, FIG. 1a), we confirmed its mitochondrial localization. Next, mitochondria were isolated and SIRT4-EGFP and its interactions characterized by immunoaffinity purification-mass spectrometry (IP-MS)[19,20]. 106 SIRT4 protein partners achieved computationally-assessed SAINT significance (FIG. 9 8 including known interactions and substrates GLUD1, IDE and MLYCD[6,16,21]. We hypothesized that unrecognized substrates were present in our dataset, and interrogated SIRT4 interactions using bioinformatics to extract metabolic pathways and functional networks that were enriched. Notably, pyruvate metabolism, the TCA cycle, branched-chain amino acid catabolism, and biotin metabolism were significantly enriched (FIG. 4B and FIG. 4C). Interaction of SIRT4 with biotin-dependent carboxylases has been reported[22], validating the reliability of our dataset.

Strikingly, we found that SIRT4 associated with all three of the multimeric mammalian dehydrogenase complexes—PDH, oxoglutarate dehydrogenase (OGDH), and branched-chain alpha-keto acid dehydrogenase (BCKDHA) complexes (FIG. 1B). These complexes occupy discrete positions within the cellular metabolic landscape, regulating TCA cycle activity and amino acid metabolism (FIG. 1C). Given its relative prominence within SIRT4 interactions, we focused on PDH. Currently, PDH is known to be regulated by reversible phosphorylation (20, 21) and acetylation of its E1 component (22, 23), with its activity playing a central role in coupling metabolic flux from glycolysis into either the TCA cycle or fatty acid synthesis. We confirmed that SIRT4-EGFP immuno-isolated (FIG. 1D) and co-localized (FIG. 1E) with DLAT and PDH component X (PDHX), the E2 and E3-binding components of the PDHC, respectively (see FIG. 1b).). Furthermore, in wild-type (WT) cells we confirmed the interaction of DLAT with endogenous SIRT4 by reciprocal IP (FIG. 1f). Given this confirmatory evidence, we next tested whether these proteins were biological substrates of SIRT4.

Figures 1, 2:
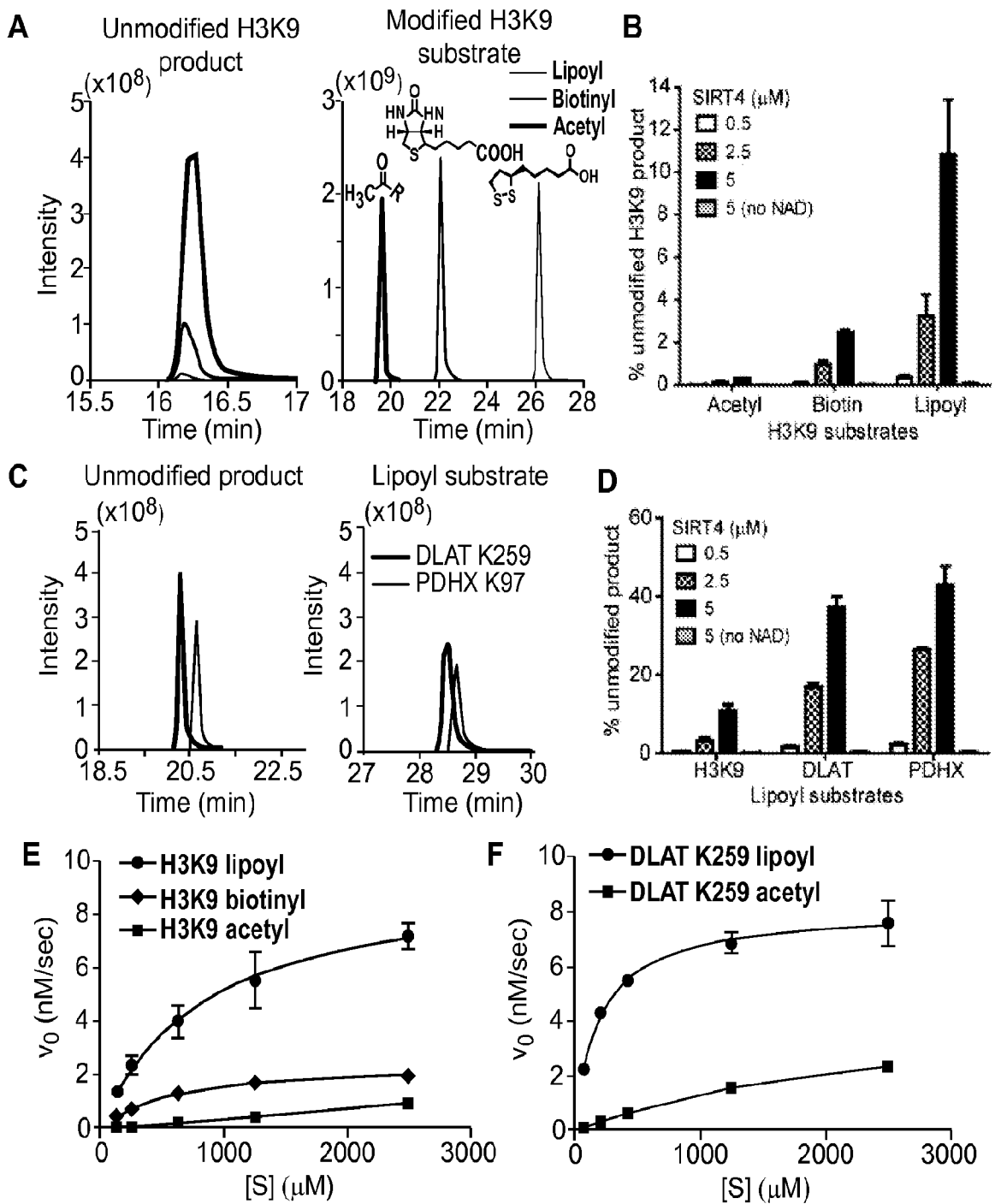
FIG. 2. SIRT4 hydrolyzes lipoyl-, biotin-, and acetyl-lysine modifications in vitro. a, Representative extracted ion chromatograms show unmodified H3K9 product after incubation of SIRT4 with various acyl-modified H3K9 peptides. Unreacted substrate peaks are labeled with corresponding acyl functional group. b, SIRT4 more efficiently catalyzes removal of lipoyl- and biotinyl-modifications from H3K9 (SEQ ID NOs: 3 and 4, respectively) than acetyl (SEQ ID NO: 5) in a NAD-dependent manner (mean±S.E.M.; n=3). c, Representative extracted ion chromatograms show SIRT4 activity for lipoyl-modified mitochondrial substrates, DLAT and PDHX. d, Compared to H3K9, SIRT4 generates increased unmodified product when reacted with DLAT and PDHX (mean±S.E.M.; n=3). e and f, Steady-state kinetic analysis of SIRT4 with H3K9 and DLAT peptide substrates show increased catalytic efficiency for lipoyl-modified substrates (mean±S.D.; n=2, except for H3K9 lipoyl (SEQ ID NO: 3) where n=3). g, Recombinant SIRT4 (5 μM) was incubated with various acyl-modified H3K9 peptides (10 μM) with or without NAD (1 mM), and product and residual substrate peptides detected by LC-MS after reaction. Representative extracted ion chromatograms show unreacted acyl-modified H3K9 substrates (S), and unmodified H3K9 products (SEQ ID NO: 6) (P, ~16.5 min) only when NAD was added. h, The percentage of unmodified peptide in each reaction was calculated. SIRT4 more efficiently catalyzes removal of lipoyl-(SEQ ID NO: 3) and biotinyl (SEQ ID NO: 4)-modifications than acetyl H3K9 (SEQ ID NO: 5). Compared to H3K9-modified substrates, SIRT4 activity for lipoyl-modified mitochondrial substrate DLAT (SEQ ID NO: 11) and PDHX (SEQ ID NO: 13) peptides is enhanced, showing increased unmodified product after reaction (mean±S.E.M.; n=3). i, Extracted ion chromatograms of unreacted lipoyl-modified DLAT (SEQ ID Nos: 7-9) and PDHX (SEQ ID NO: 12) peptide substrates (S) and unmodified products (P) following incubation with SIRT4. j-l, Comparison of SIRT3 (0.5 μM) and SIRT4(0.5 μM) initial velocity versus [5] for DLAT K259 (j) acetyl (SEQ ID NO: 10) and (1) lipoyl peptide (SEQ ID NO: 8). k, Impact of SIRT4, H161Y or PDP1 on PDH activity, measured using a PDH immunocapture colorimetric assay (reduction of NAD$^+$ to NADH). In parallel, phosphorylation of all three phospho-serine PDH-E1 sites was assessed by western blotting; E1—loading control.
Figure 2:
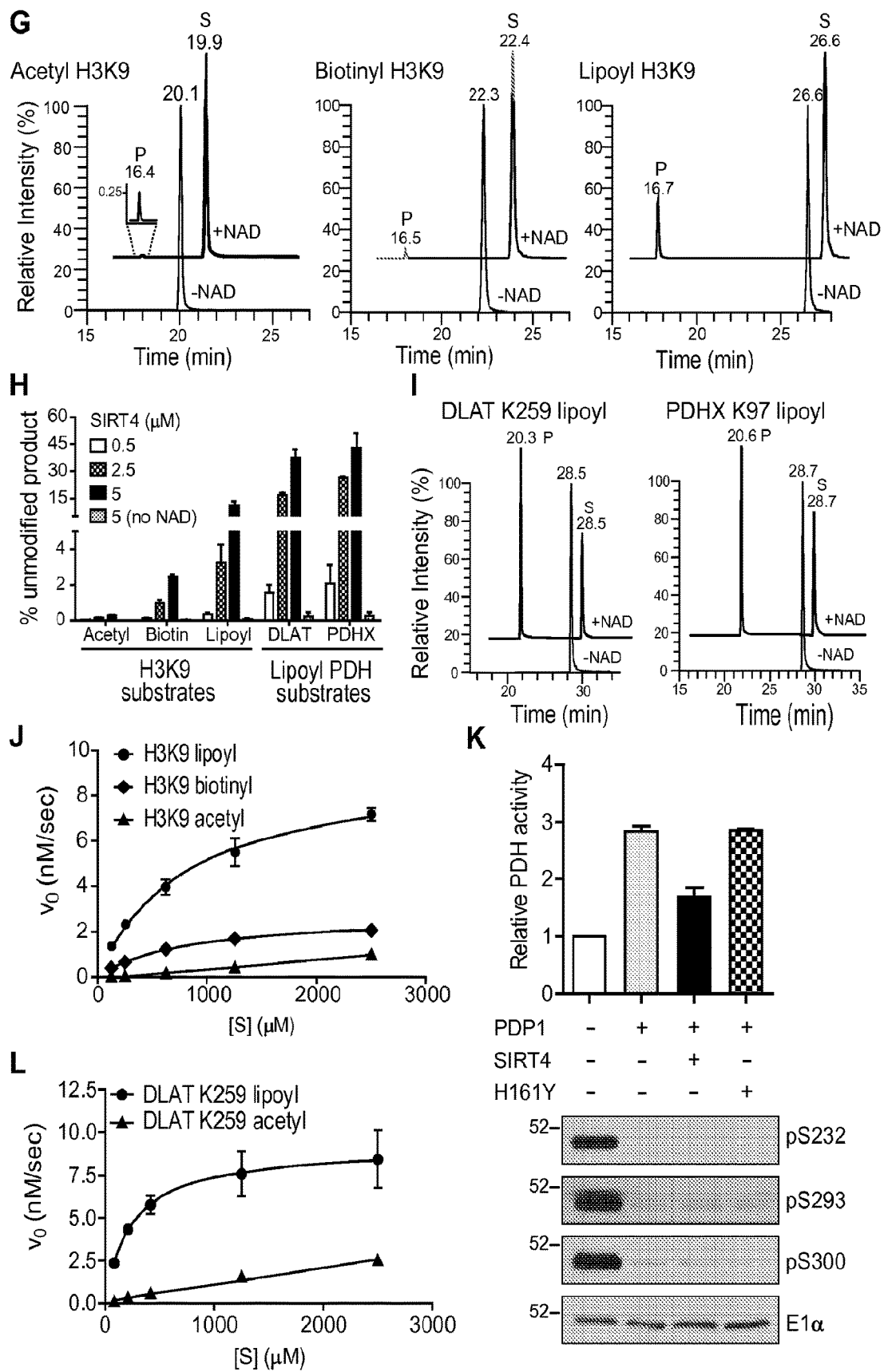
Figures 2, 5:
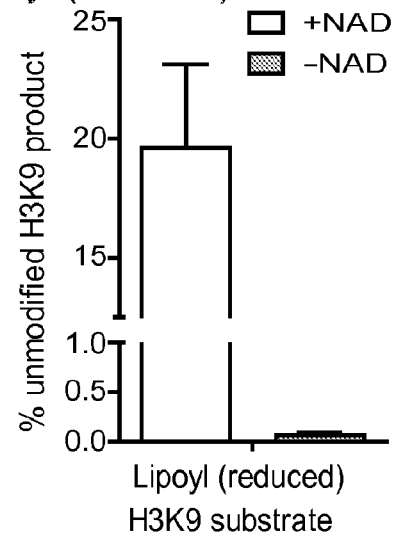
FIG. 5. In vitro substrate specificity of SIRT4. a, Representative MS/MS spectra confirming that the product generated from reaction of acyl H3K9 peptides with SIRT4+NAD was the unmodified H3K9 peptide (SEQ ID NO: 6) (See FIG. 2g; P, 16.5 min). b, Reaction of various acyl-modified H3K9 peptides with the recombinant SIRT4 H161Y catalytic mutant did not generate significant unmodified peptide products. c, Linear regression of v on SIRT4] vs. [5] for the reaction of SIRT4 with either H3K9 acetyl (SEQ ID NO: 5) or MCD acetyl was performed to estimate the katIK,r, parameter. d, Representative MS/MS spectra confirming that the product generated from the reaction of the lipoyl-modified DLAT peptide with SIRT4+NAD was the unmodified DLAT (see FIG. 2il P, 20.3 min). e, Representative MS/MS spectra confirming that the product generated from the reaction of the lipoyl-modified PDHX peptide with SIRT4+NAD was the unmodified PDHX peptide (FIG. 2i; P, 20.6 min.). f, SIRT4 also hydrolyzed reduced lipoamide modifications in an NAD-dependant manner.

The lipoamide cofactor bound to E2 (transferase enzymes) is required for dehydrogenase complex activity (FIG. 1b). Given that other mitochondrial SIRTs can hydrolyze various ε-amino group lysine modifications[3,4] and that all PDHC components were present in our SIRT4 isolation, we speculated that E2 dehydrogenase components may be biological substrates of SIRT4, and that SIRT4 may directly hydrolyze the lipoamid modification. To test this we screened the in vitro activity of recombinant SIRT4 against differentially-modified synthetic peptides (FIG. 10). Firstly, SIRT4 activity towards acyl-modified H3K9 peptides (SEQ ID NOs: 3-5) was measured using a liquid-chromatography (LC)-MS-based deacylation assay. SIRT4 was incubated with H3K9 peptides modified with acetyl-lysine (SEQ ID NO: 5), biotinyl-lysine (SEQ ID NO: 4) or lipoyl-lysine (SEQ ID NO: 3), in the presence or absence of NAD. Following reaction, the remaining unreacted substrates and newly generated unmodified peptides were identified and quantified by LC-MS (FIGS. 2A, 2G-2I and FIG. 5). SIRT4 only exhibited enzymatic activity in the presence of NAD (FIG. 2G), demonstrated by the generation of a product peak (P) at 16.5 min retention time that was confirmed by MS-based sequencing to be unmodified H3K9 product (FIG. 5A). Thus, SIRT4 was able to hydrolyze all three modifications, as well as reduced lipoamide H3K9 peptide (FIG. 5F). To compare the relative preference of SIRT4 for these different substrates, we used extracted ion chromatograms to quantify unreacted substrate (S) and product (P) amounts from all reactions, and represented the percentage of unmodified peptide generated (FIG. 2H). SIRT4 showed the highest potency for removing the lipoyl modification. The relative amount of unmodified product generated using 5 μM SIRT4 was 11% (lipoyl—SEQ ID NO: 3), 3% (biotinyl—SEQ ID NO: 4) and 0.3% (acetyl—SEQ ID NO: 3) (FIG. 2B and FIG. 2H, H3K9 substrates). To determine the critical residues for SIRT4 enzymatic function, we performed the same deacylation assays using catalytically inactive SIRT4, containing the H161Y point mutation, and observed no significant activity for any of these substrates (FIG. 5B). In vitro, SIRT4 activity towards the reduced lipoamide H3K9 was reported recently; however activity shown was not reproducible[18] and at very low levels (possibly due to the difficulty with purifying recombinant SIRT4). Importantly, the endogenous biological substrates remain unknown. We next tested whether SIRT4 could remove lipoamide from putative mitochondrial substrate peptides DLAT (SEQ ID NO: 11) and PDHX (SEQ ID NO: 13) (FIGS. 2D, 2H and 2I). Indeed, SIRT4 showed greater activity towards these substrates than H3K9, as the proportion of unmodified peptide generated following reaction increased (FIG. 2c and FIG. 2i) increased to 33% for DLAT (SEQ ID NO: 11) and 42% for PDHX (SEQ ID NO: 13) (FIG. 2h, lipoyl PDH substrates). With promising enzymatic activity identified using the LC-MS deacylation assay, we next performed steady-state enzyme kinetic assays.

SIRT4's catalytic efficiency towards the various acyl-modified peptide substrates was assessed (Table 1 below).

We also compared SIRT4's ability to deacetylate biological substrate MCD[16], and found that SIRT4 was ~1270-fold more efficient at hydrolyzing the DLAT lipoamide (Table 1, FIG. 5C and FIG. 13A). Lastly, we evaluated the ability of the other mitochondrial SIRTs to hydrolyze lipoyl (SEQ ID NO: 8) or acetyl (SEQ ID NO: 10) modifications from DLAT. For SIRT5, low, but detectable activity was measured for DLAT acetyl (SEQ ID NO: 10) (FIG. 13B), while no activity was detected for DLAT lipoyl (SEQ ID NO: 8) reactions (FIG. 13E). SIRT3 showed some enzymatic activity towards DLAT lipoyl (SEQ ID NO: 8) (FIG. 13C), however, this efficiency was 13-fold lower than for DLAT acetyl (SEQ ID NO: 10) (FIGS. 13D and E). Thus, SIRT4 has the highest catalytic efficiency for lipoamide modifications compared to the other mitochondrial SIRTs. The observed SIRT4 $k_{cat}/K_m$ kinetics may reflect the biological conditions within PDH. For example, each of the DLAT lipoyl domains is concentrated within PDH at >1 mM[23,24], supporting a potential cellular role for SIRT4 lipoamidase activity in regulating PDH activity. Collectively, our in vitro kinetic assays demonstrate that, compared to deacetylation, SIRT4 has superior lipoamidase and biotinylase activity. Interestingly, there is precedence for one single enzyme to have activity for both modifications in serum[25]; however, a mammalian cellular lipoamidase has not yet been identified until this study.

To characterize the impact of the observed in vitro activity, we next assessed whether SIRT4 could regulate the activity of PDH. We first used an immuno-capture assay to test the activity of purified porcine PDH in vitro (FIG. 14A). Purified PDH was treated with pyruvate dehydrogenase phosphatase catalytic subunit 1 (PDP1), followed by either SIRT4 or inactive SIRT4 H161Y protein. As expected, PDP1

| Peptide substrate | Sequence | $k_{cat}$ (s$^{-1}$) | $K_m$ (μM) | $k_{cat}/K_m$ (s$^{-1}$M$^{-1}$) |
| --- | --- | --- | --- | --- |
| H3 K9 Acetyl | KQTARKSTGGWW SEQ ID NO: 5) | ND* | ND* (>2500) | 0.083 ± 0.004 |
| H3 K9 Biotinyl | | 0.0005 ± 0.0001 | 719 ± 79 | 0.74 ± 0.05 |
| H3 K9 Lipoyl | | 0.0019 ± 0.0002 | 814 ± 163 | 2.30 ± 0.30 |
| DLAT K259 Acetyl | EIETDKATIGW SEQ ID NO: 10) | 0.0011 ± 0.0001 | ND* (>2500) | 0.20 ± 0.01 |
| DLAT K259 Lipoyl | | 0.0016 ± 0.0001 | 239 ± 51 | 7.65 ± 1.31 |
| MCD K471 Acetyl | SYLGSKNIKASEW SEQ ID NO: 29 | ND* | ND* (>2500) | 0.0064 ± 0.0006 |

Synthetic peptide sequences are shown containing the modified lysine residues (underlined) as indicated by peptide substrate.
*ND, $k_{cat}$ and $K_m$ could not be determined because $v_0$ versus [S] was linear.
$K_{cat}/K_m$ was calculated by linear regression of $v_0$/[SIRT4] versus [S].
SIRT4 enzyme concentration = 5 μM.

Compared to acetylated H3K9 (SEQ ID NO: 5), SIRT4 removed biotinyl (SEQ ID NO: 4) (11-fold) and lipoyl (SEQ ID NO: 3 (30-fold) modifications more efficiently (FIG. 2e and FIG. 9). The DLAT lipoyl peptide (SEQ ID NO: 8) displayed a 3.5-fold increased efficiency compared to H3K9 lipoyl (SEQ ID NO: 3), owing mainly to a decreased $K_m$ (FIG. 2f and FIG. 9).

In another experiment, SIRT4 removed lipoyl (28-fold) and biotinyl (9-fold) H3K9 modifications (SEQ ID NOs: 3 and 4, respectively) more efficiently (FIG. 2j and Table 1). The DLAT lipoyl peptide (SEQ ID NO: 8) displayed a 3.3-fold increase in efficiency compared to H3K9 lipoyl (SEQ ID NO: 3), owing mainly to a decreased Km (FIGS. 2j and 2k and Table 1). While SIRT4 showed slightly greater efficiency towards DLAT acetyl (SEQ ID NO: 10) compared to H3K9 acetyl (SEQ ID NO: 5), this efficiency was still 38-fold lower than DLAT lipoyl (SEQ ID NO: 8) (FIG. 2l).

elevated PDH activity via removal of phosphorylation from all three inhibitory PDH-E1α sites (FIG. 2K). Notably, only active SIRT4 was able to attenuate PDH activity, and this was not due to increased phosphorylation of E1 (FIG. 2K). Therefore, we speculated that the reduction in activity may result from SIRT4 directly hydrolyzing the DLAT lipoamide.

Figures 1, 3:
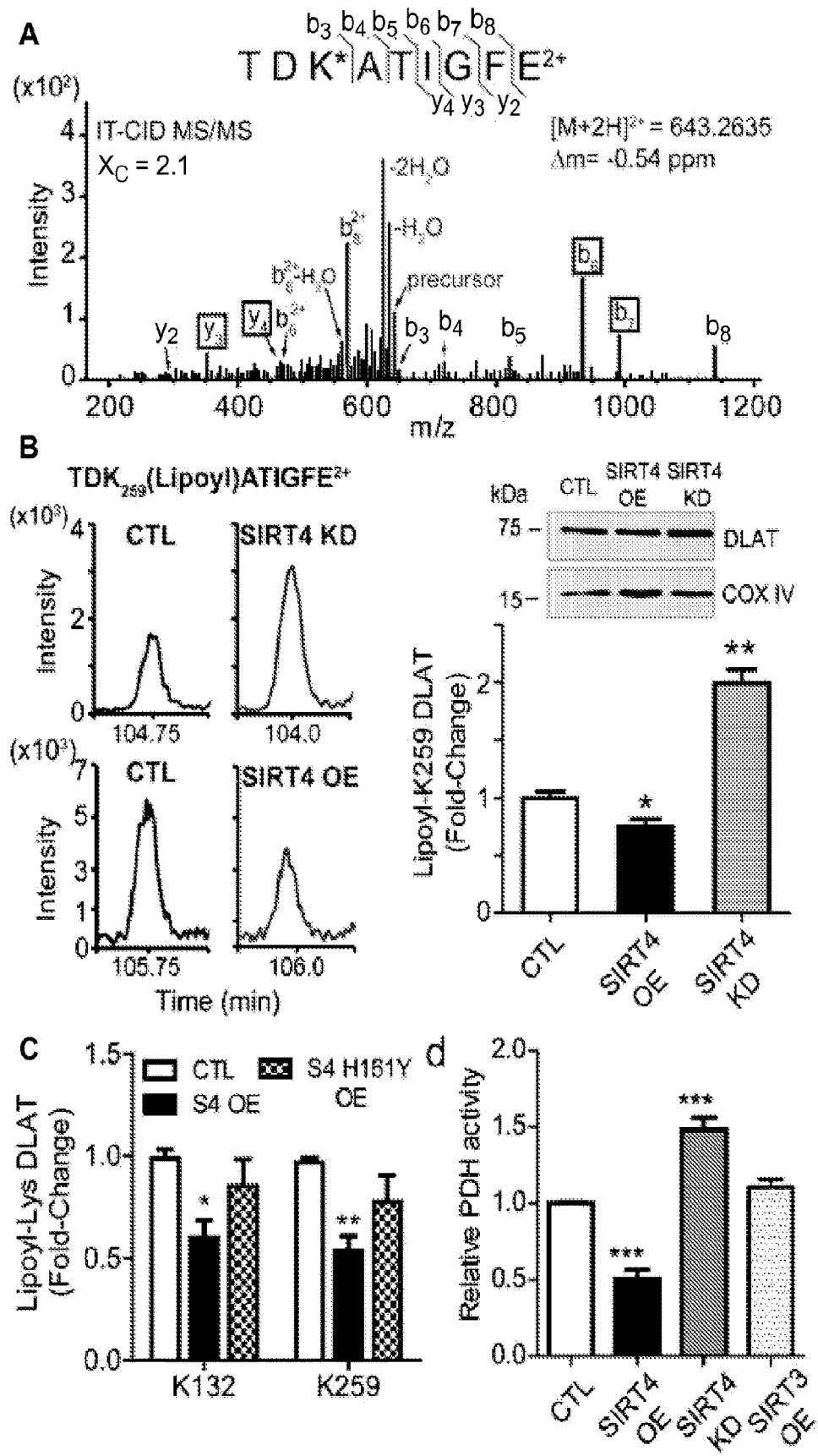
FIG. 3. SIRT4 regulates cellular activity of the pyruvate dehydrogenase complex. a, Tandem MS identification of endogenous DLAT peptide containing lipoyl-K259 (SEQ ID NO: 8) isolated from MRC5 mitochondria. Boxed product ions were used for SRM-based lipoyl assay. b, SIRT4-dependent modulation of DLAT lipoyl-K259 (SEQ ID NO: 8). Stable over-expression of SIRT4 (SIRT4-OE) in MRC5 cells decreased DLAT lipoamide levels, while stable knock-down of SIRT4 (SIRT4-KD) elevated levels as detected by SRM-based quantification. (Left panel) Representative precursor-product extracted ion chromatograms summed from individual fragment traces. (Right panel) Mean fold-change of DLAT lipoyl-K259 (SEQ ID NO: 8) levels versus control (CTL) (mean±S.E.M; n=6, SIRT4-OE vs CTL; n=3, SIRT4-KD vs CTL; *p=0.02, **p=0.007). c, Mean fold-change of DLAT lipoyl-lysine (versus CTL) after transient expression of SIRT4 (*p=0.02, K132; p=0.005, K259) and SIRT4 H161Y catalytic mutant in HEK293 cells (mean±S.E.M.; n=3). d, Relative PDHC activity is regulated by SIRT4 but not by SIRT3. SIRT4-OE impaired PDH activity, while SIRT4-KD enhanced activity versus control. Relative activity is calculated from the slope of linear regression of $A_{450}$ colorimetric reporter ($A_{450\ nm}$), which is coupled to reduction of NAD$^+$ to NADH (mean±S.E.M.; n=3, SIRT4-KD and SIRT3-OE; n=6, IRT4-OE; *p<0.05 by one-way ANOVA). e, PDH activity in fibroblasts expressing SIRT proteins measured by PDH immunocapture colorimetric assay, in comparison to GFP cells (CTL) (mean±S.E.M.; n=3 SIRTs 3-5; n=5 GFP; ****p<0.0001). f, Impact of SIRT4 or catalytic mutant H161Y overexpression on inhibitory PDH-E1 phosphorylation. E1 is loading control. g, Levels of lipoylated DLAT in cells overexpressing mitochondrial SIRTs. DLAT and COX IV are loading controls. h, SIRT4-dependent modulation of DLAT lipoyl K132 and K259 detected by PRM quantification (mean±S.E.M; n=3, *p=0.03, ***p=0.0003). i, Time-course of PDH activity in wild-type MRC5 cells stimulated with glutamax (4 mM), compared to unstimulated cells (mean±S.E.M.; n=4 2D and 3D, p<0.0001; n=3 8D, p=0.0007). j, Phosphorylation of regulatory PDH-E1 sites and total E1 (loading control), and endogenous SIRT4, DLAT, and COX IV (loading control) levels, following glutamax stimulation. k, Time-course of DLAT lipoyl levels (K132 and K259) measured by PRM quantification in cells stimulated with glutamax versus unstimulated (mean±S.E.M.; n=3) for 2 days (ns), 3 days (*p=0.015), and 8 days (**p=0.007, *p=0.018). l, PDH activity in cells with knock-down levels of endogenous SIRT4 (shSIRT4#1 or #5, mean±S.E.M; n=4) treated with glutamax (4 mM for 8 days), compared to control shCTL cells (mean±S.E.M; n=7, *p<0.0001). m, PDH activity from mouse liver mitochondria of Sirt4$^{-/-}$ mice (mean±S.E.M, n=3, *p<0.039) versus wild-type control (n=4).
Figures 2, 3:
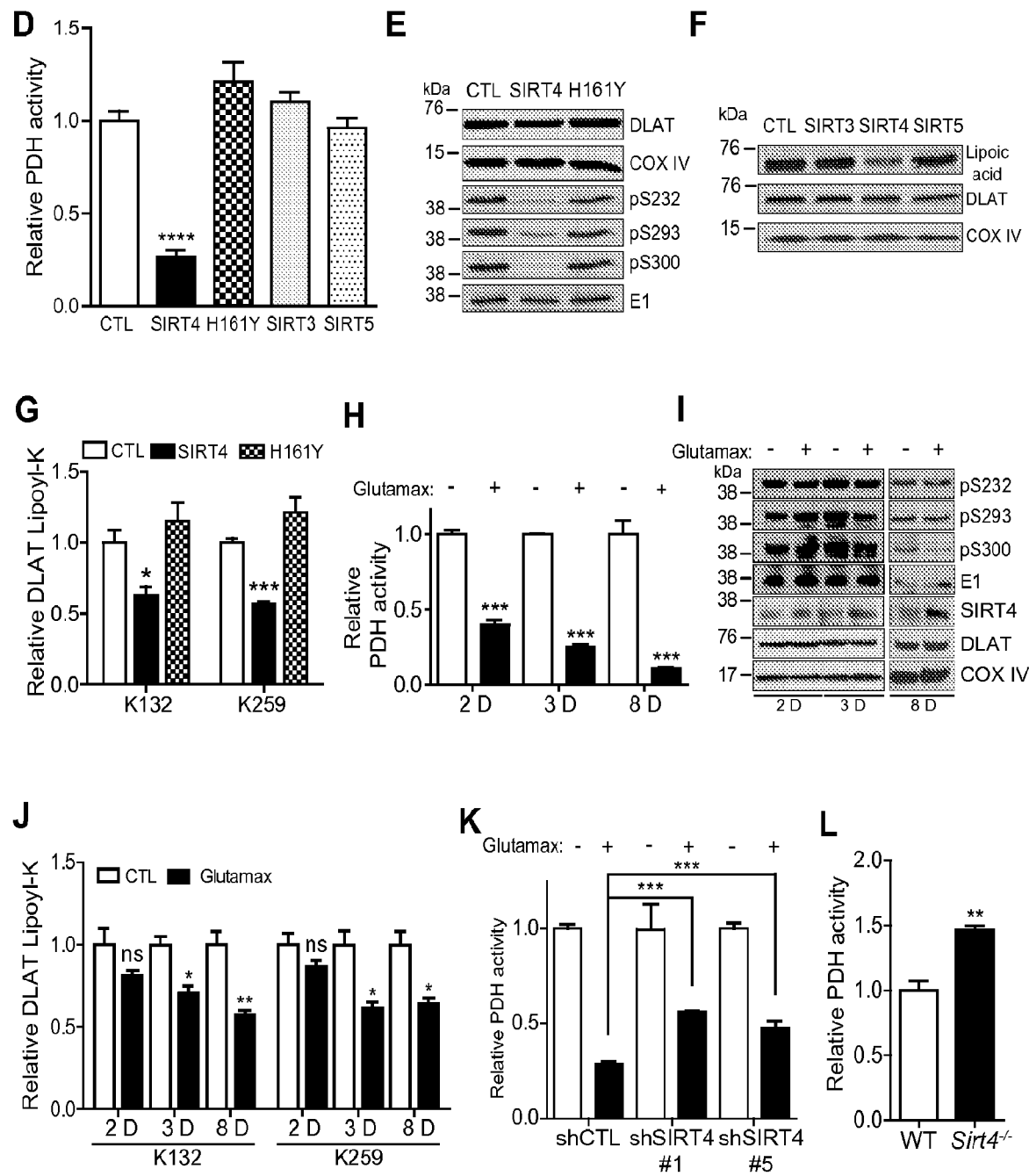
Figures 2, 6:
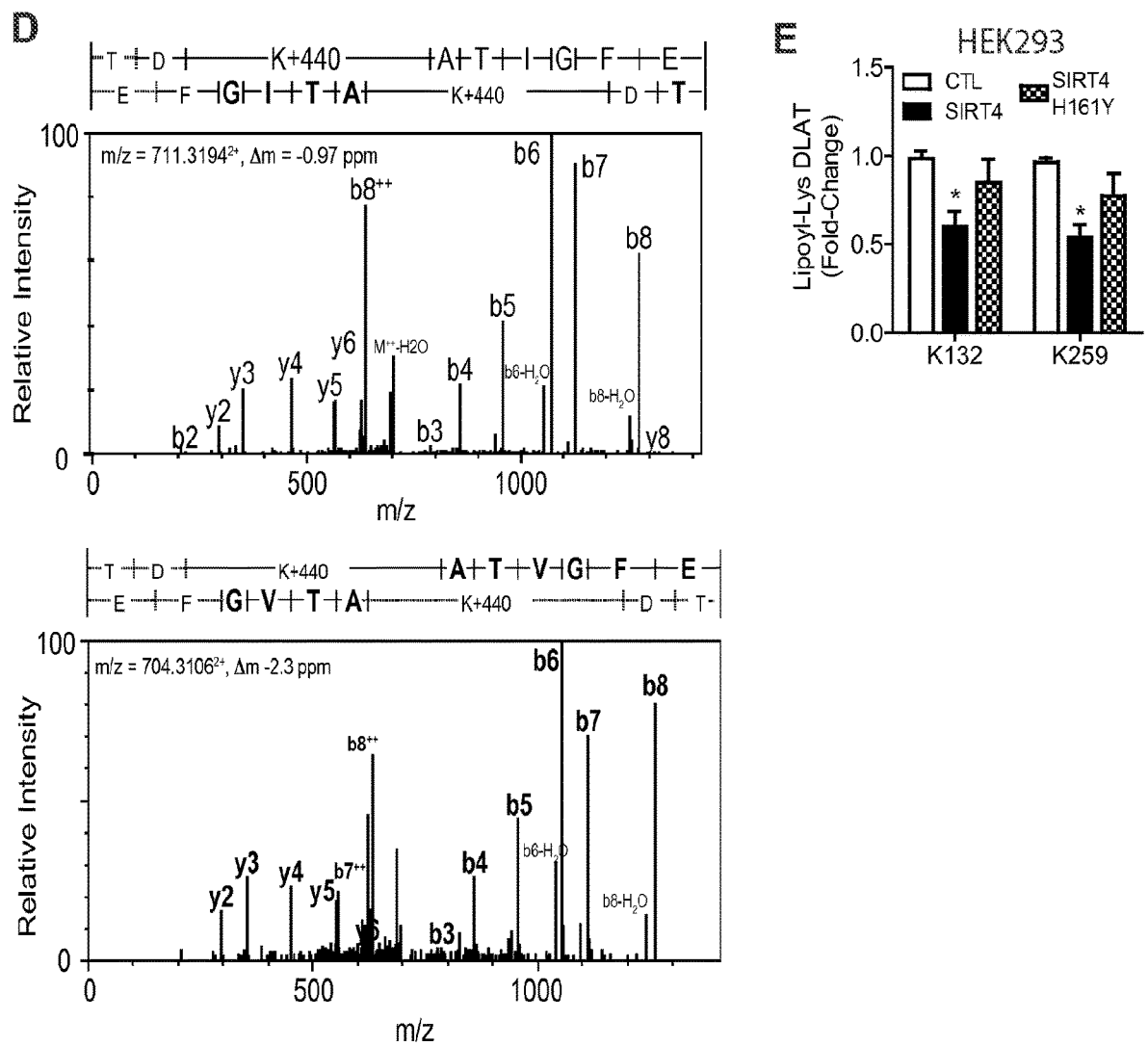
FIG. 6. MS-based quantification of DLAT lipoyl-lysine in mitochondria. a, Representative MS/MS spectra of K132-lipoyl peptide acquired from endogenous DLAT that was immuno-affinity purified from MRC5 mitochondria and digested with endoproteinase GluC. b, Representative MS/MS spectra of chemically synthesized K259 lipoyl peptide (SEQ ID NO: 8). Synthetic peptides displayed similar retention time and fragmentation pattern as the endogenous DLAT K259 lipoyl peptide (SEQ ID NO: 8). c, Representative individual precursor-product extracted ion chromatograms for y3, y4, b5, and b6 ions, which were summed and used for relative quantification of SIRT4-dependent modulation of DLAT lipoyl-K259 (SEQ ID NO: 8). d, Representative MS/MS spectra of endogenous DLAT peptide containing K259 lipoyl (top) and K132 lipoyl (bottom) detected from endogenous DLAT present in mitochondrial lysates that were digested with endoproteinase GluC. *Reduced and alkylated with N-ethylmaleimde ($\Delta m=440$ amu vs. unmodified lysine). e, Relative levels of DLAT lipoyl-lysine (versus CTL) following transient expression of SIRT4 or SIRT4 H161Y catalytic mutant in HEK293 cells (mean±S.E.M.; n=3; *p=0.02, K132; *p=0.01, K259).

Given that the lipoamide essential cofactor required for acetyl-CoA production[26,27], we hypothesized that SIRT4 may regulate PDH function. To test this endogenously, we measured the relative levels of DLAT lipoyl following manipulation of cellular SIRT4 expression. Without lipoamide antibodies, we designed a targeted, quantitative LC-selected reaction monitoring (SRM)-MS-based assay[28]. Endogenous DLAT was subjected to IP-MS analysis, and proteotypic peptides containing lipoyl-K259f (FIG. 3a) and lipoyl-K132 (FIG. 6A) were identified. A synthetic lipoyl- K259 peptide (SEQ ID NO: 8) showed a similar retention time and fragmentation pattern (FIG. 6B) compared to the endogenous lipoyl-K259 peptide (FIG. 3a), further validating implementation in our LC-SRM assays. Next, we generated stable MRC5 fibroblasts with knock-down SIRT4 expression (SIRT4-KD) using several shRNA constructs (FIG. 11, SEQ ID NOs: 14-18); construct #5 (SEQ ID NO: 18) achieved >80% knock-down (FIG. 7). Using our LC-SRM-MS assay, we measured the relative levels of DLAT lipoyl-K259 in mitochondrial lysates from SIRT4-KD cells compared to cells over-expressing (OE) SIRT4-EGFP (SIRT4-OE), and control cells expressing EGFP (CTL) (FIG. 6C). SIRT4-OE reduced DLAT lipoyl-K259 (SEQ ID NO 8), while SIRT4-KD elevated the modification levels compared to CTL cells (FIG. 3b). Manipulation of cellular SIRT4 levels did not significantly change DLAT steady-state levels (FIG. 3b). This demonstrated that SIRT4 modulates cellular levels of lipoylated DLAT in MRC5 fibroblasts. We next tested whether SIRT4-mediated regulation of DLAT lipoyl was manifested in HEK293 cells transiently transfected with mCherry (CTL, control), SIRT4, or SIRT4 H161Y. Consistent with our observations in fibroblasts, SIRT4-OE diminished levels of DLAT lipoyl-K259 (SEQ ID NO: 8) (FIG. 3c). Moreover, due to increased PDHC abundance in kidney cells, we could also reliably quantify SIRT4-OE-mediated reduction of DLAT lipoyl-K132 (SEQ ID NO: 7) (FIG. 3c). Importantly, these effects were specific to active SIRT4, as expression of the SIRT4 H161Y mutant did not significantly alter lipoyl levels at these sites.

Figure 14:
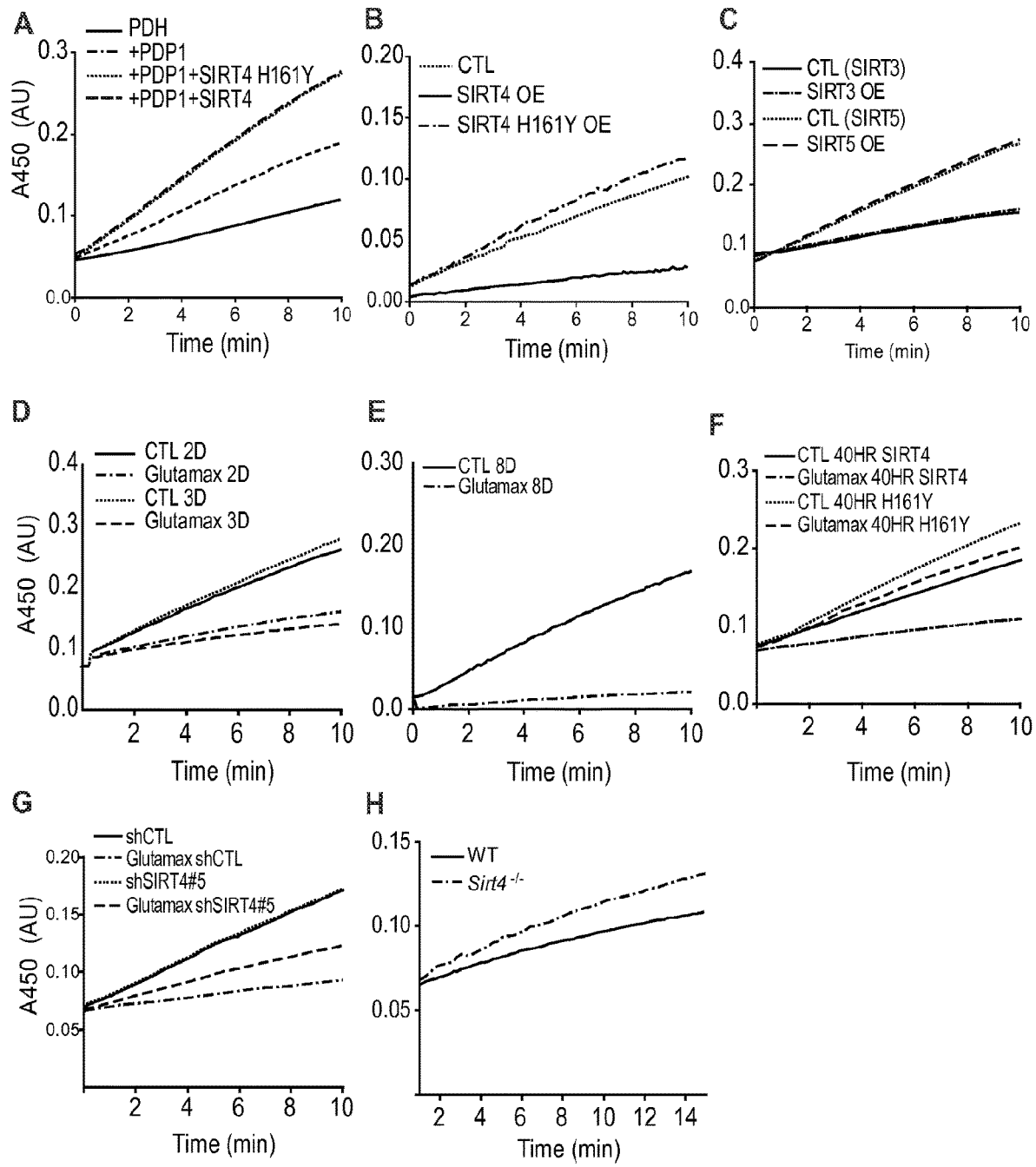
FIG. 14. SIRT4-dependent modulation of PDH complex activity. PDH activity was measured following immuno-capture of intact PDH in a microwell plate. The ability of bound PDHC to reduce NAD+ to NADH was coupled to production of reporter dye that was detected by absorbance at 450 nm over time. Slope of linear regression curves was used to calculate relative PDH activity. (A) Recombinant SIRT4 can inhibit purified porcine PDH. (B) Over-expression of active SIRT4 in cells also inhibits endogenous PDH activity, but not the catalytic mutant H161Y. (C) Over-expression of SIRT3 or SIRT5 in fibroblasts does not change cellular PDH activity. (D-E) Time-course of cells stimulated with glutamax exhibit increased PDH inhibition. (F) Cells over-expressing active SIRT4 have increased PDH inhibition compared to cells over-expressing the catalytic mutant H161Y after 40 hr culture in glutamax containing medium. (G) shRNA-mediated knockdown of SIRT4 (construct #5) impairs the inhibition of PDH after 8 day glutamax stimulation. (H) Mouse liver mitochondria from Sirt4−/− animals have increased PDH activity compared to wild-type control animals.
Figure 16:
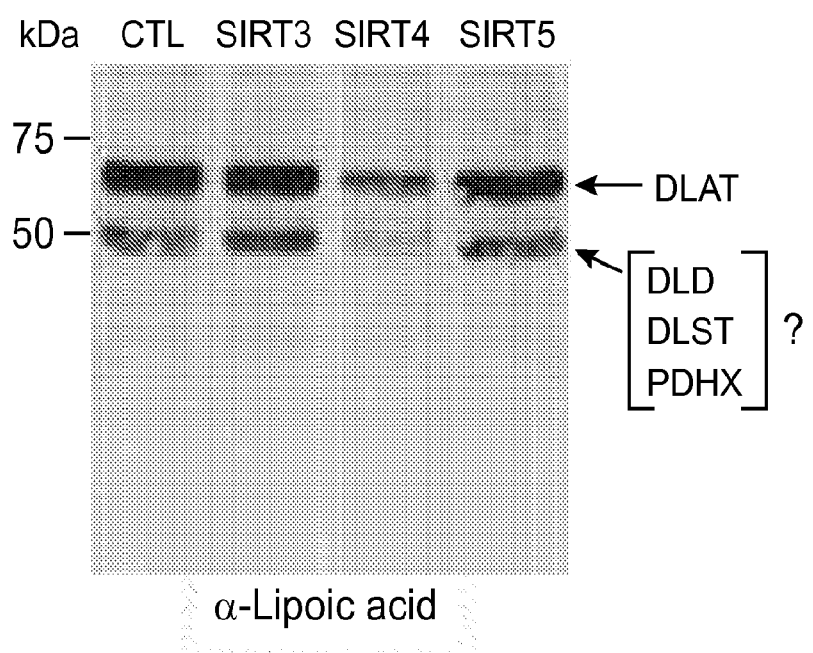
FIG. 16 provides a representative full western blot, illustrating immunoreactive bands for lipoyl in whole-cell extracts of fibroblasts expressing elevated levels of GFP (CTL), SIRT3, SIRT4, or SIRT5. *refers to peptides (other than DLAT) having a lipoyl modification.

In another experiment, we examined the impact of SIRT levels on the endogenous cellular activity of PDH by over-expressing (OE) each of the mictochondrial SIRTs in cultured human fibroblasts (absolute PDH activity is represented in FIG. 14). Strikingly, PDH activity was only diminished in fibroblasts stably expressing SIRT4 when compared to cells over-expressing GFP (CTL, control), SIRT3, or SIRT5 (FIG. 3e and FIG. 14b). Despite SIRT3 displaying marginal in vitro enzymatic activity for the DLAT-lipoamide peptide (FIG. 13C), OE of either SIRT3 or SIRT5 did not alter cellular PDH activity (FIG. 2e and FIG. 14c), reinforcing the cellular specificity of SIRT4. Moreover, PDH activity was not reduced following overexpression of SIRT4 H161Y, demonstrating the involvement of active SIRT4. To further characterize the correlation between SIRT4 OE and the decrease in PDH activity and lipoyl levels, we measured phosphorylation of PDH-E1. Interestingly, we observed reduced phosphorylation at all three sites in SIRT4 OE cells (FIG. 3F). Reduced phosphorylation would be expected to activate PDH; however, this result demonstrates that PDH activity can be inhibited independently of kinase-mediated phosphorylation. Therefore, if SIRT4 reduces DLAT lipoamide levels and, thereby, kinase binding sites, kinase function could also be impaired. We next measured the relative levels of DLAT lipoyl in these cells. We observed reduced DLAT lipoyl levels in SIRT4 OE cells, but not in cells OE SIRT3 or SIRT5 (FIG. 3G). To measure the impact of SIRT4 on site-specific levels of DLAT lipoyl-lysine, we developed targeted quantitative LC-MS-based parallel reaction monitoring (PRM) assays (31). This assay requires unique DLAT lipoyl peptides, which we determined by LC-MS/MS analysis of DLAT immunopurified from fibroblast mitochondria. By comparing the fragmentation patterns of the endogenous DLAT peptide and a chemically synthesized analog, the K259 lipoyl (SEQ ID NO: 8) was validated (FIGS. 15A-B). We also confirmed the DLAT lipoylation at K132 (SEQ ID NO: 7) (FIG. 15C). This targeted PRM assay allowed us to measure the effect of SIRT4 OE on the relative levels of DLAT K132 lipoyl (SEQ ID NO: 7) and K259 lipoyl (SEQ ID NO: 8) in mitochondrial lysates (FIGS. 3H and 6D). Consistent with the results from western blotting (FIG. 3G), only expression of active SIRT4 reduced levels of DLAT lipoyl when compared to H161Y or the control (FIG. 3H). This reduction in DLAT lipoyl was not due to altered DLAT steady-state levels (FIG. 3F). To ensure that the ability of SIRT4 to modulate DLAT lipoyl was not cell-type specific or an artifact from cell line generation, we performed the PRM assay on HEK293 cells transiently transfected with either mCherry (CTL), SIRT4, or SIRT4 H161Y. Consistently, only expression of active SIRT4 diminished levels of DLAT lipoyl (FIG. S6E).

Finally, we investigated whether augmented DLAT lipoyl levels affected overall PDHC activity in fibroblasts. PDHC activity was measured following immuno-capture from SIRT4-OE, -KD, and CTL cells. PDHC isolated from SIRT4-OE cells with decreased DLAT lipoyl, displayed impaired PDHC activity relative to control (FIG. 3A and FIG. 8A). Additionally, PDHC isolated from SIRT4-KD cells harboring increased DLAT lipoyl, exhibited enhanced PDH activity (FIG. 3B, and FIG. 8B). As SIRT4 is thought to interact with SIRT3 (although we did not identify this in our interaction study, FIG. 9), we tested the effect of SIRT3-OE on PDH activity. In contrast to our results in SIRT4-OE, SIRT3-OE marginally, though not significantly, increased PDH activity (FIG. 3D and FIG. 8B), indicating specific attenuation by SIRT4. Together, these experiments show that SIRT4 regulates levels of lipoyl-containing DLAT, thereby controlling PDHC activity. Our findings suggest that SIRT4 can negatively regulate production of acetyl-CoA through inactivation of PDH, providing an additional mechanism to that reported via inhibition of MDC[16].

We next investigated a cellular condition known to inhibit PDH activity, and examined the involvement of SIRT4 in this process. Glutamine stimulation in rat liver is known to cause an increased flux through OGDH and decreased flux through PDH, leading to PDH inhibition (32). Stimulation of WT fibroblasts with the glutamine supplement glutamax (4 mM) caused a significant time-dependent decrease in PDH activity (FIG. 3I, FIG. 14D-E). Importantly, this reduction in activity was not due to increased levels of inhibitory PDH-E1 phosphorylation, relative to unstimulated cells at the same time points (FIG. 3J). While steady-state levels of DLAT were unchanged due to glutamax stimulation (FIG. 3J), a decrease in DLAT lipoyl levels was observed within 48 hr (FIG. 3K). In agreement with these observations, we detected elevated expression of endogenous SIRT4 in cells stimulated with glutamax (FIG. 3J). To validate the dependence of PDH inhibition on SIRT4 activity, we first measured PDH activity in SIRT4 OE cells stimulated with glutamax. Following 40 hr culture in glutamax, over-expression of active SIRT4 triggered pronounced PDH inhibition when compared to the catalytic mutant (FIG. 54J). Next, to test the specific involvement of endogenous SIRT4, we generated fibroblasts with knock-down SIRT4 expression using shRNA (FIG. 11). Effective SIRT4 knock-down was confirmed at mRNA level by qPCR (shSIRT4#1 (SEQ ID NO: 14) and #5 (SEQ ID NO: 18) achieving >75% knock-down) (FIG. 7B) and at protein level (FIG. 7C). Importantly, SIRT4 knock-down led to a partial rescue of the glutamax-mediated inhibition of PDH activity, and this observation was consistent for both shRNAs tested (FIG. 3L and FIG. 14G). It remains to be determined whether residual SIRT4 still functions in these knocked-down lines to decrease PDH activity following glutamax stimulation, or another yet to be identified PDH inhibition mechanism is at play. Finally, to confirm the role of SIRT4 in vivo, we isolated fresh liver mitochondria from SIRT4 knock-out (KO) mice and tested PDH activity. Indeed, we observed elevated PDH activity in SIRT4 KO mice relative to control mice (FIG. 3M, FIG. 14H). Altogether, these data demonstrate that endogenous SIRT4 is involved in inhibiting PDH activity in vivo.

In summary, the data provided herein demonstrates a physical and functional interaction between SIRT4 and mitochondrial PDH constituents. We demonstrate that SIRT4 catalytic efficiency for biotinyl- and lipoyl-lysine modifications is far superior compared to its deacetylation activity. The PDH E2 component DLAT is a biological substrate of SIRT4, with SIRT4 directly regulating the levels of K132 and K259 lipoamide modifications. Until now, PDH activity was thought to be principally inhibited by kinase-dependent phosphorylation. However, the data provided herein shows that SIRT4 can directly hydrolyze the lipoamide from DLAT to impair the functional activity of the complex. Furthermore, glutamine stimulation induces SIRT4 and inhibits PDH activity, while SIRT4 KO mice exhibit increased PHD activity. As this complex controls pyruvate decarboxylation fueling multiple downstream pathways, the data provided herein highlight SIRT4 as a critical regulator of cellular metabolism.

REFERENCES

1 Guarente, L. Sir2 links chromatin silencing, metabolism, and aging. Genes Dev. 14, 1021-1026 (2000).
2 Imai, S., Armstrong, C. M., Kaeberlein, M. & Guarente, L. Transcriptional silencing and longevity protein Sir2 is an NAD-dependent histone deacetylase. Nature 403, 795-800 (2000).
3 Jiang, H. et al. SIRT6 regulates TNF-alpha secretion through hydrolysis of long-chain fatty acyl lysine. Nature 496, 110-113 (2013).
4 Du, J. et al. Sirt5 is a NAD-dependent protein lysine demalonylase and desuccinylase. Science 334, 806-809 (2011).
5 Peng, C. et al. The first identification of lysine malonylation substrates and its regulatory enzyme. Mol. Cell. Proteomics 10, M111 012658 (2011).
6 Haigis, M. C. et al. SIRT4 inhibits glutamate dehydrogenase and opposes the effects of calorie restriction in pancreatic beta cells. Cell 126, 941-954 (2006).
7 Linn, T. C., Pettit, F. H. & Reed, L. J. Alpha-keto acid dehydrogenase complexes. X. Regulation of the activity of the pyruvate dehydrogenase complex from beef kidney mitochondria by phosphorylation and dephosphorylation. Proc. Natl. Acad. Sci. U.S.A. 62, 234-241 (1969).
8 Wieland, O. & Jagow-Westermann, B. ATP-dependent inactivation of heart muscle pyruvate dehydrogenase and reactivation by Mg(++). FEBS Lett. 3, 271-274 (1969).
9 Verdin, E., Hirschey, M. D., Finley, L. W. & Haigis, M. C. Sirtuin regulation of mitochondria: energy production, apoptosis, and signaling. Trends Biochem. Sci. 35, 669-675 (2010).
10 Lombard, D. B. et al. Mammalian Sir2 homolog SIRT3 regulates global mitochondrial lysine acetylation. Mol. Cell. Biol. 27, 8807-8814 (2007).
11 Csibi, A. et al. The mTORC1 pathway stimulates glutamine metabolism and cell proliferation by repressing SIRT4. Cell 153, 840-854 (2013).
12 Jeong, S. M. et al. SIRT4 has tumor-suppressive activity and regulates the cellular metabolic response to DNA damage by inhibiting mitochondrial glutamine metabolism. Cancer Cell 23, 450-463 (2013).
13 Newman, J. C., He, W. & Verdin, E. Mitochondrial protein acylation and intermediary metabolism: regulation by sirtuins and implications for metabolic disease. J. Biol. Chem. 287, 42436-42443 (2012).
14 Lin, H., Su, X. & He, B. Protein lysine acylation and cysteine succination by intermediates of energy metabolism. ACS Chem. Biol. 7, 947-960 (2012).
15 Michishita, E., Park, J. Y., Burneskis, J. M., Barrett, J. C. & Horikawa, I. Evolutionarily conserved and nonconserved cellular localizations and functions of human SIRT proteins. Mol. Biol. Cell 16, 4623-4635 (2005).
16 Laurent, G. et al. SIRT4 coordinates the balance between lipid synthesis and catabolism by repressing malonyl CoA decarboxylase. Mol. Cell 50, 686-698 (2013).
17 Rauh, D. et al. An acetylome peptide microarray reveals specificities and deacetylation substrates for all human sirtuin isoforms. Nat Commun 4, 2327 (2013).
18 Feldman, J. L., Baeza, J. & Denu, J. M. Activation of the protein deacetylase SIRT6 by long-chain fatty acids and widespread deacylation by mammalian sirtuins. J. Biol. Chem. 288, 31350-31356 (2013).
19 Joshi, P. et al. The functional interactome landscape of the human histone deacetylase family. Mol. Syst. Biol. 9, 672 (2013).
20 Tsai, Y. C., Greco, T. M., Boonmee, A., Miteva, Y. & Cristea, I. M. Functional proteomics establishes the interaction of SIRT7 with chromatin remodeling complexes and expands its role in regulation of RNA polymerase I transcription. Mol. Cell. Proteomics 11, 60-76 (2012).
21 Ahuja, N. et al. Regulation of insulin secretion by SIRT4, a mitochondrial ADP-ribosyltransferase. J. Biol. Chem. 282, 33583-33592 (2007).
22 Wirth, M. et al. Mitochondrial SIRT4-type proteins in *Caenorhabditis elegans* and mammals interact with pyruvate carboxylase and other acetylated biotin-dependent carboxylases. Mitochondrion (2013).
23 Roche, T. E. et al. Sizing of bovine heart and kidney pyruvate dehydrogenase complex and dihydrolipoyl transacetylase core by quasielastic light scattering. Biochemistry (Mosc.) 32, 5629-5637 (1993).
24 Wagenknecht, T., Grassucci, R., Radke, G. A. & Roche, T. E. Cryoelectron microscopy of mammalian pyruvate dehydrogenase complex. J. Biol. Chem. 266, 24650-24656 (1991).
25 Nilsson, L. & Kagedal, B. Co-purification of human serum lipoamidase and biotinidase: evidence that the two enzyme activities are due to the same enzyme protein. Biochem. J. 291 (Pt 2), 545-551 (1993).
26 Perham, R. N. Domains, motifs, and linkers in 2-oxo acid dehydrogenase multienzyme complexes: a paradigm in the design of a multifunctional protein. Biochemistry (Mosc.) 30, 8501-8512 (1991).
27 Zhou, Z. H., McCarthy, D. B., O'Connor, C. M., Reed, L. J. & Stoops, J. K. The remarkable structural and functional organization of the eukaryotic pyruvate dehydrogenase complexes. Proc. Natl. Acad. Sci. U.S.A 98, 14802-14807 (2001).
28 Picotti, P. & Aebersold, R. Selected reaction monitoring-based proteomics: workflows, potential, pitfalls and future directions. Nat. Methods 9, 555-566 (2012).
29 Cristea, I. M., Williams, R., Chait, B. T. & Rout, M. P. Fluorescent proteins as proteomic probes. Mol. Cell. Proteomics 4, 1933-1941 (2005).
30 Ishihama, Y., Rappsilber, J. & Mann, M. Modular stop and go extraction tips with stacked disks for parallel and multidimensional Peptide fractionation in proteomics. J. Proteome Res. 5, 988-994 (2006).

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

Any single embodiment herein may be supplemented with one or more element from any one or more other embodiment herein.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A method of assaying lipoamidase activity of human SIRT4 in a mammalian cell sample that expresses a human SIRT4 comprising measuring a level of a dihydrolipoyllysine acetyltransferase (DLAT) lipoamide peptide comprising the amino acid sequence TDK[lipoyl]AT in a cell that expresses the human SIRT4, thereby assaying the lipoamidase activity of human SIRT4 in the cell.

2. The method of claim 1, that is an in vitro method.

3. The method of claim 1, wherein the cell comprises a decreased level of the DLAT lipoamide peptide compared to a cell of the same type that does not express a SIRT4 polypeptide.

4. The method of claim 1, wherein the DLAT lipoamide peptide is selected from the group consisting of DLAT lipoyl-K259 (SEQ ID NO: 8) and DLAT lipoyl-K132 (SEQ ID NO: 7).

5. The method of claim 1, wherein the cell expresses an endogenous human SIRT4 polypeptide.

6. The method of claim 1, wherein the cell is engineered to express a human SIRT4 polypeptide.

7. The method of claim 6, wherein the cell is engineered to express a SIRT4 polypeptide comprising amino acids 33-314 of SEQ ID NO: 2 and lacks amino acids 1-32 of SEQ ID NO: 2.

8. The method of claim 6, wherein the cell is engineered to express a human SIRT4 polypeptide comprising the amino acid sequence set forth in SEQ ID NO: 2.

9. The method of claim 1, wherein the measuring step comprises measuring relative abundance of the DLAT lipoamide in a sample using mass spectrometry.

10. The method of claim 9, wherein the mass spectrometry is single step mass spectrometry (MS) or tandem mass spectrometry (MS/MS) analysis.

11. The method of claim 9, wherein mass spectrometry analysis is a targeted mass spectrometry approach.

12. The method of claim 9, wherein the mass spectrometry is selection reaction monitoring (SRM) mass spectrometry or parallel reaction monitoring (PRM).

* * * * *